US008900282B2

(12) United States Patent
Brawn

(10) Patent No.: US 8,900,282 B2
(45) Date of Patent: Dec. 2, 2014

(54) LIGHT THERAPY APPARATUS AND METHODS

(71) Applicant: Biolux Research Ltd., Vancouver (CA)

(72) Inventor: Peter Brawn, Vancouver (CA)

(73) Assignee: Biolux Research Ltd., Vancouver (CA)

( * ) Notice: Subject to any disclaimer, the term of this patent is extended or adjusted under 35 U.S.C. 154(b) by 0 days.

(21) Appl. No.: 13/895,330

(22) Filed: May 15, 2013

(65) Prior Publication Data

US 2013/0253620 A1  Sep. 26, 2013

Related U.S. Application Data

(63) Continuation of application No. 11/767,302, filed on Jun. 22, 2007, now abandoned, which is a continuation-in-part of application No. 11/335,583, filed on Feb. 16, 2006, now abandoned.

(60) Provisional application No. 60/705,753, filed on Aug. 5, 2005, provisional application No. 60/653,828, filed on Feb. 17, 2005.

(51) Int. Cl.
*A61N 5/06* (2006.01)

(52) U.S. Cl.
CPC ....... *A61N 5/0613* (2013.01); *A61N 2005/0647* (2013.01); *A61N 2005/0652* (2013.01); *A61N 2005/0659* (2013.01)
USPC .......................................................... 607/88

(58) Field of Classification Search
USPC ..................................... 607/88–94; 606/2–19
See application file for complete search history.

(56) References Cited

U.S. PATENT DOCUMENTS

| 2,635,175 A | 4/1953 | Wilson |
| 2,884,926 A | 5/1959 | Grasso |
| 3,516,411 A | 6/1970 | Adler |
| 3,971,387 A | 7/1976 | Mantell |
| 4,244,373 A | 1/1981 | Nachman |
| 4,273,535 A | 6/1981 | Yamamoto et al. |

(Continued)

FOREIGN PATENT DOCUMENTS

| CA | 2212010 | 8/1996 |
| CA | 2439882 | 9/2002 |

(Continued)

OTHER PUBLICATIONS

Office Action for U.S. Appl. No. 13/826,383, mailed Sep. 5, 2013, 10 pages.

(Continued)

*Primary Examiner* — Aaron Roane
(74) *Attorney, Agent, or Firm* — Cooley LLP

(57) ABSTRACT

An extra-oral light therapy device comprises a support that registers against features of a patient's head. A light source is mounted to the support. The light source may comprise an array of light emitting diodes ("LEDs"). A controller controls the extra-oral light therapy device. The support may comprise a tray fitted to the patient's teeth or a head-set fitted to the patient's ears and the bridge of the patient's nose. An external light therapy device has a thin, molded substrate, at least one array of light emitters mounted onto the thin, molded substrate, an attaching means for removably attaching the device to an area of treatment, and a controller for controlling the external light therapy device. Methods for supporting light sources adjacent desired treatment locations and for treating jaw bone disorders and jaw osteonecrosis and biostimulating bone and soft tissue are also disclosed.

36 Claims, 8 Drawing Sheets

(56) References Cited

U.S. PATENT DOCUMENTS

| | | |
|---|---|---|
| 4,457,707 A | 7/1984 | Smiley et al. |
| 4,628,931 A | 12/1986 | Barrett |
| 4,840,174 A | 6/1989 | Gluckman |
| 4,877,401 A | 10/1989 | Higuchi et al. |
| 4,983,381 A | 1/1991 | Torres Zaragoza |
| 5,259,380 A | 11/1993 | Mendes et al. |
| 5,358,503 A | 10/1994 | Bertwell et al. |
| 5,365,624 A | 11/1994 | Berns |
| 5,421,727 A | 6/1995 | Stevens et al. |
| 5,429,501 A | 7/1995 | Farzin-Nia et al. |
| 5,445,608 A | 8/1995 | Chen et al. |
| 5,487,662 A | 1/1996 | Kipke et al. |
| 5,500,009 A | 3/1996 | Mendes et al. |
| 5,549,660 A | 8/1996 | Mendes et al. |
| 5,601,619 A | 2/1997 | Drechsler |
| 5,611,793 A | 3/1997 | Wilson et al. |
| 5,616,140 A | 4/1997 | Prescott |
| 5,660,461 A | 8/1997 | Ignatius et al. |
| 5,683,436 A | 11/1997 | Mendes et al. |
| 5,709,645 A | 1/1998 | Siever |
| 5,766,233 A | 6/1998 | Thiberg |
| 5,814,039 A | 9/1998 | Prescott |
| 5,913,883 A | 6/1999 | Alexander et al. |
| 5,951,141 A | 9/1999 | Bradley |
| 5,989,245 A | 11/1999 | Prescott |
| 6,063,108 A | 5/2000 | Salansky et al. |
| 6,077,073 A | 6/2000 | Jacob |
| 6,096,066 A | 8/2000 | Chen et al. |
| 6,156,028 A | 12/2000 | Prescott |
| 6,210,162 B1 | 4/2001 | Chishti et al. |
| 6,217,325 B1 | 4/2001 | Chishti et al. |
| 6,290,714 B1 | 9/2001 | Streeter |
| 6,319,273 B1 | 11/2001 | Chen et al. |
| 6,328,732 B1 | 12/2001 | Donitzky et al. |
| 6,366,802 B1 | 4/2002 | Haber et al. |
| 6,398,548 B1 | 6/2002 | Muhammad et al. |
| 6,413,267 B1 | 7/2002 | Dumoulin-White et al. |
| 6,418,345 B1 | 7/2002 | Tepper et al. |
| 6,450,170 B1 | 9/2002 | Friedman |
| 6,454,791 B1 | 9/2002 | Prescott |
| 6,471,716 B1 | 10/2002 | Pecukonis |
| 6,494,900 B1 | 12/2002 | Salansky et al. |
| 6,514,075 B1 | 2/2003 | Jacob |
| 6,524,329 B1 | 2/2003 | Benedict |
| 6,537,305 B1 | 3/2003 | Thiberg |
| 6,554,611 B2 | 4/2003 | Chishti et al. |
| 6,602,275 B1 | 8/2003 | Sullivan |
| 6,616,447 B1 | 9/2003 | Rizoiu et al. |
| 6,626,666 B2 | 9/2003 | Chishti et al. |
| 6,629,840 B2 | 10/2003 | Chishti et al. |
| 6,645,230 B2 | 11/2003 | Whitehurst |
| 6,648,639 B2 | 11/2003 | Mao |
| 6,648,904 B2 | 11/2003 | Altshuler et al. |
| 6,663,659 B2 | 12/2003 | McDaniel |
| 6,676,655 B2 | 1/2004 | McDaniel |
| 6,678,562 B1 | 1/2004 | Tepper et al. |
| 6,699,037 B2 | 3/2004 | Chishti et al. |
| 6,722,880 B2 | 4/2004 | Chishti et al. |
| 6,743,249 B1 | 6/2004 | Alden |
| 6,746,473 B2 | 6/2004 | Shanks et al. |
| 6,832,912 B2 | 12/2004 | Mao |
| 6,896,693 B2 | 5/2005 | Sullivan |
| 6,942,658 B1 | 9/2005 | Rizoiu et al. |
| 6,974,224 B2 | 12/2005 | Thomas-Benedict |
| 6,976,841 B1 | 12/2005 | Osterwalder |
| 6,986,782 B2 | 1/2006 | Chen et al. |
| 7,018,395 B2 | 3/2006 | Chen |
| 7,029,276 B2 | 4/2006 | Mao |
| 7,070,611 B2 | 7/2006 | Biel |
| 7,081,128 B2 | 7/2006 | Hart et al. |
| 7,084,389 B2 | 8/2006 | Spector |
| 7,100,615 B1 | 9/2006 | Kert |
| 7,101,384 B2 | 9/2006 | Benedict |
| 7,134,874 B2 | 11/2006 | Chishti et al. |
| 7,163,400 B2 | 1/2007 | Cozean et al. |
| 7,184,614 B2 | 2/2007 | Slatkine |
| 7,201,577 B2 | 4/2007 | Levine |
| 7,223,270 B2 | 5/2007 | Altshuler et al. |
| 7,223,281 B2 | 5/2007 | Altshuler et al. |
| 7,244,253 B2 | 7/2007 | Neev |
| 7,306,620 B2 | 12/2007 | Cumbie |
| 7,329,273 B2 | 2/2008 | Altshuler et al. |
| 7,329,274 B2 | 2/2008 | Altshuler et al. |
| 7,335,025 B2 | 2/2008 | Levine |
| 7,354,448 B2 | 4/2008 | Altshuler et al. |
| 7,374,569 B2 | 5/2008 | Whatcott et al. |
| 7,422,598 B2 | 9/2008 | Altshuler et al. |
| D582,559 S | 12/2008 | Khawaled et al. |
| 7,474,307 B2 | 1/2009 | Chishti et al. |
| 7,513,906 B2 | 4/2009 | Passy et al. |
| 7,597,497 B2 | 10/2009 | Levine |
| 7,751,895 B2 | 7/2010 | Jones et al. |
| 7,775,795 B2 | 8/2010 | Khawaled et al. |
| D636,074 S | 4/2011 | Levine |
| 8,021,148 B2 | 9/2011 | Goodson et al. |
| 8,029,278 B1 | 10/2011 | Levine |
| 8,105,080 B2 | 1/2012 | Chishti et al. |
| D661,806 S | 6/2012 | Khawaled et al. |
| 8,214,958 B2 | 7/2012 | Pinyayev et al. |
| 8,215,954 B2 | 7/2012 | Levine |
| 8,240,312 B2 | 8/2012 | Feuerstein et al. |
| 8,262,306 B2 | 9/2012 | Levine |
| 8,262,390 B1 | 9/2012 | Levine |
| 8,267,609 B2 | 9/2012 | Levine |
| 8,371,853 B2 | 2/2013 | Levine |
| 8,562,340 B2 | 10/2013 | Chishti et al. |
| 8,591,227 B2 | 11/2013 | Levine |
| 8,636,506 B2 | 1/2014 | Pavlin |
| 2002/0165583 A1 | 11/2002 | Tepper et al. |
| 2002/0198575 A1 | 12/2002 | Sullivan |
| 2003/0009205 A1 | 1/2003 | Biel |
| 2003/0125782 A1 | 7/2003 | Streeter |
| 2003/0130709 A1 | 7/2003 | Haber et al. |
| 2003/0167080 A1 | 9/2003 | Hart et al. |
| 2003/0186193 A1 | 10/2003 | Comfort |
| 2004/0043349 A1 | 3/2004 | Liao |
| 2004/0093042 A1 | 5/2004 | Altshuler et al. |
| 2004/0093047 A1 | 5/2004 | Lach |
| 2004/0127961 A1 | 7/2004 | Whitehurst |
| 2004/0147984 A1 | 7/2004 | Altshuler et al. |
| 2004/0193235 A1 | 9/2004 | Altshuler et al. |
| 2004/0199227 A1 | 10/2004 | Altshuler et al. |
| 2004/0230259 A1 | 11/2004 | Di Matteo |
| 2004/0248059 A1 | 12/2004 | Katsuda et al. |
| 2005/0004631 A1 | 1/2005 | Benedict |
| 2005/0070977 A1 | 3/2005 | Molina |
| 2005/0080404 A1 | 4/2005 | Jones et al. |
| 2005/0181333 A1 | 8/2005 | Karazivan et al. |
| 2005/0202363 A1 | 9/2005 | Osterwalder |
| 2005/0203592 A1 | 9/2005 | Teichert |
| 2005/0221251 A1 | 10/2005 | Soukos et al. |
| 2005/0278003 A1 | 12/2005 | Feldman |
| 2005/0279949 A1 | 12/2005 | Oldham et al. |
| 2005/0282102 A1 | 12/2005 | Kert |
| 2006/0009823 A1 | 1/2006 | Richardson et al. |
| 2006/0061986 A1 | 3/2006 | Kuo et al. |
| 2006/0085052 A1 | 4/2006 | Feuerstein et al. |
| 2006/0200212 A1 | 9/2006 | Brawn |
| 2006/0223032 A1 | 10/2006 | Fried et al. |
| 2006/0228158 A1 | 10/2006 | Levine et al. |
| 2007/0105212 A1 | 5/2007 | Oldham et al. |
| 2007/0110683 A1 | 5/2007 | Levine et al. |
| 2007/0121786 A1 | 5/2007 | Okawa et al. |
| 2007/0129776 A1 | 6/2007 | Robins et al. |
| 2007/0166666 A1 | 7/2007 | Levine |
| 2007/0183988 A1 | 8/2007 | Prosise et al. |
| 2007/0185553 A1 | 8/2007 | Kennedy |
| 2007/0208289 A1 | 9/2007 | Walther et al. |
| 2007/0208395 A1 | 9/2007 | Leclerc et al. |
| 2007/0219605 A1 | 9/2007 | Yaroslavsky et al. |
| 2007/0248930 A1 | 10/2007 | Brawn |
| 2007/0259310 A1 | 11/2007 | Goodson et al. |
| 2007/0265605 A1 | 11/2007 | Vaynberg et al. |
| 2008/0032252 A1 | 2/2008 | Hayman et al. |

(56) References Cited

U.S. PATENT DOCUMENTS

| | | | |
|---|---|---|---|
| 2008/0051858 | A1 | 2/2008 | Haber et al. |
| 2008/0077199 | A1 | 3/2008 | Shefi et al. |
| 2008/0113313 | A1 | 5/2008 | Khouri |
| 2008/0214530 | A1 | 9/2008 | Colles |
| 2008/0227046 | A1 | 9/2008 | Lowe et al. |
| 2008/0227047 | A1 | 9/2008 | Lowe et al. |
| 2008/0254401 | A1 | 10/2008 | Yazdi |
| 2008/0255498 | A1 | 10/2008 | Houle |
| 2008/0273163 | A1 | 11/2008 | Sasaki |
| 2009/0011380 | A1 | 1/2009 | Wang |
| 2009/0029311 | A1 | 1/2009 | Chan |
| 2009/0240310 | A1 | 9/2009 | Kennedy |
| 2009/0323370 | A1 | 12/2009 | Koo |
| 2010/0055634 | A1 | 3/2010 | Spaulding et al. |
| 2010/0086891 | A1 | 4/2010 | Jun |
| 2010/0094190 | A1 | 4/2010 | Walther et al. |
| 2010/0305668 | A1 | 12/2010 | Brawn |
| 2010/0318161 | A1 | 12/2010 | Brawn |
| 2011/0091835 | A1 | 4/2011 | Levine |
| 2011/0104633 | A1 | 5/2011 | Levine |
| 2011/0136070 | A1 | 6/2011 | Rubin et al. |
| 2011/0136071 | A1 | 6/2011 | Levens |
| 2011/0159549 | A1 | 6/2011 | Oldham et al. |
| 2011/0183296 | A1 | 7/2011 | Levine |
| 2012/0009539 | A1 | 1/2012 | Goodson et al. |
| 2012/0040300 | A1 | 2/2012 | Levens et al. |
| 2012/0094246 | A1 | 4/2012 | Pavlin |
| 2012/0148975 | A1 | 6/2012 | Brawn |
| 2012/0148976 | A1 | 6/2012 | Brawn |
| 2012/0183919 | A1 | 7/2012 | Levine |
| 2013/0034859 | A1 | 2/2013 | Boege et al. |
| 2013/0196284 | A1 | 8/2013 | Brawn |
| 2013/0280671 | A1 | 10/2013 | Brawn et al. |
| 2013/0289674 | A1 | 10/2013 | Brawn |
| 2014/0072932 | A1 | 3/2014 | Brawn et al. |
| 2014/0080082 | A1 | 3/2014 | Lowe |
| 2014/0121731 | A1 | 5/2014 | Brawn |

FOREIGN PATENT DOCUMENTS

| | | |
|---|---|---|
| CA | 2448385 | 11/2002 |
| CA | 2505559 | 5/2004 |
| CA | 2515695 | 10/2004 |
| CA | 2598189 | 8/2006 |
| EP | 2110159 | 10/2009 |
| GB | 2203649 | 10/1988 |
| GB | 2212010 | 7/1989 |
| GB | 2335363 | 9/1999 |
| GB | 2360461 | 9/2001 |
| GB | 2376891 | 12/2002 |
| GB | 2416311 | 1/2006 |
| JP | 2004-202189 | 7/2004 |
| RU | 2133630 | 7/1999 |
| WO | WO 95/10243 | 4/1995 |
| WO | WO 02/24052 | 3/2002 |
| WO | WO 02/062419 | 8/2002 |
| WO | WO 2004/075985 | 9/2004 |
| WO | WO 2005/015291 | 2/2005 |
| WO | WO 2005/062710 | 7/2005 |
| WO | WO 2005/107637 | 11/2005 |
| WO | WO 2006/028461 | 3/2006 |
| WO | WO 2006/052682 | 5/2006 |
| WO | WO 2006/087633 | 8/2006 |
| WO | WO 2006/098719 | 9/2006 |
| WO | WO 2006/115765 | 11/2006 |
| WO | WO 2007/007335 | 1/2007 |
| WO | WO 2007/007336 | 1/2007 |
| WO | WO 2007/014217 | 2/2007 |
| WO | WO 2007/025244 | 3/2007 |
| WO | WO 2007/047892 | 4/2007 |
| WO | WO 2007/062251 | 5/2007 |
| WO | WO 2007/085776 | 8/2007 |
| WO | WO 2007/092368 | 8/2007 |
| WO | WO 2007/109245 | 9/2007 |
| WO | WO 2007/121760 | 11/2007 |
| WO | WO 2008/001388 | 1/2008 |
| WO | WO 2008/092660 | 8/2008 |
| WO | WO 2008/114255 | 9/2008 |
| WO | WO 2009/000075 | 12/2008 |
| WO | WO 2009/072108 | 6/2009 |
| WO | WO 2009/123965 | 10/2009 |
| WO | WO 2009/158297 | 12/2009 |
| WO | WO 2010/093632 | 8/2010 |
| WO | WO 2010/108080 | 9/2010 |
| WO | WO 2010/142013 | 12/2010 |
| WO | WO 2010/142031 | 12/2010 |
| WO | WO 2011/056260 | 5/2011 |
| WO | WO 2012/048423 | 4/2012 |
| WO | WO 2012/075584 | 6/2012 |
| WO | WO 2013/155366 | 10/2013 |
| WO | WO 2013/155632 | 10/2013 |

OTHER PUBLICATIONS

Hsieh, F. Y. et al., "Sample-size calculations for the Cox proportional hazards regression model with nonbinary covariates," Controlled Clinical Trials, 21(6):552-560 (2000).

Moher, D. et al., "CONSORT 2010 Explanation and Elaboration: Updated guidelines for reporting parallel group randomised trial," BMJ, 340:c869 (2010), 28 pages.

Pandis, N. et al., "External apical root resorption in patients treated with conventional and self-ligating brackets," American Journal of Orthodontics and Dentofacial Orthopedics, 134(5):646-651 (2008).

Schulz, K. F. et al., "CONSORT 2010 Statement: Updated guidelines for reporting parallel group randomized trials," Annals of Internal Medicine, 152:726-732 (2010).

Schulz, K. F. et al., "CONSORT 2010 Statement: Updated guidelines for reporting parallel group randomised trials," PLoS Medicine, 7(3): e1000251. doi:10.1371/journal.pmed.1000251 (2010), 7 pages.

Office Action for U.S. Appl. No. 13/313,830, mailed Oct. 28, 2013, 16 pages.

Chamber's 21st Century Dictionary, Definition of Orthodontics, Chambers Harrap, retrieved from the internet on Oct. 17, 2013, retrieved from: http://www.credoreference.com/entry/chambdict/orthodontics (2001).

Mosby's Dental Dictionary, Definition of Orthodontics, Elsevier Health Sciences, retrieved from the internet on Oct. 17, 2013, retrieved from: http://www.credoreference.com/entry/ehsdent/orthodontics (2008).

Reply and Amendment Under 37 CFR 1.111 for U.S. Appl. No. 12/820,070, filed Aug. 20, 2013, 9 pages.

Declaration of Peter R. Brawn, D.D.S., Under 37 CFR 1.132, for U.S. Appl. No. 12/820,070, executed Aug. 20, 2013, 7 pages.

Office Action for U.S. Appl. No. 13/314,006, mailed Aug. 28, 2013, 19 pages.

International Search Report and Written Opinion for International Application No. PCT/CA2013/050302, mailed Jul. 19, 2013, 9 pages.

Abtahi, M. et al., "The effect of low level laser on condylar growth during mandibular advancement in rabbits," Head & Face Medicine, 8(4):1-5 (2012).

Dorland's Illustrated Medical Dictionary, 29th Edition, W.B. Saunders Company, p. 1851 (2000).

El-Bialy, T. et al., "Growth modification of the mandible with ultrasound in baboons: A preliminary report," American Journal of Orthodontics and Dentofacial Orthopedics, 130:435.e7-435.e14 (2006).

El-Bialy, T. et al., "Growth modification of the rabbit mandible using therapeutic ultrasound: Is it possible to enhance functional appliance results?," Angle Orthodontist, 73(6):631-639 (2003).

Fikackova, H. et al., "Effectiveness of low-level laser therapy in temporomandibular joint disorders: A placebo-controlled study," Photomedicine and Laser Surgery, 25(4):297-303 (2007).

Miloro, M. et al., "Low-level laser effect on mandibular distraction osteogenesis," J. Oral Maxillofac. Surg., 65:168-176 (2007).

Specialty Appliances Inc., Herbst Appliance Reference Manual, 1998 (available online http://www.specialtyappliances.com/files/pdfs/herbst_reference_manual.pdf), 12 pages.

(56) References Cited

OTHER PUBLICATIONS

Little, R. M., "The irregularity index: A quantitative score of mandibular anterior alignment," Am. J. Orthod., 68(5):554-563 (1975).
Supplementary European Search Report for European Application No. EP06710427, dated Mar. 13, 2008, 2 pages.
Office Action for U.S. Appl. No. 11/355,583, mailed Jul. 17, 2009, 12 pages.
Office Action for U.S. Appl. No. 11/355,583, mailed Jan. 20, 2010, 10 pages.
Office Action for U.S. Appl. No. 11/355,583, mailed Oct. 5, 2011, 14 pages.
Office Action for U.S. Appl. No. 11/355,583, mailed May 29, 2012, 10 pages.
International Search Report and Written Opinion for International Application No. PCT/IB2006/000358, mailed Jun. 20, 2006, 10 pages.
Office Action for U.S. Appl. No. 11/767,302, mailed Nov. 15, 2011, 16 pages.
Office Action for U.S. Appl. No. 11/767,302, mailed Mar. 11, 2010, 18 pages.
Office Action for U.S. Appl. No. 11/767,302, mailed Oct. 8, 2009, 20 pages.
Office Action for U.S. Appl. No. 11/767,302, mailed May 29, 2012, 13 pages.
International Search Report and Written Opinion for International Application No. PCT/CA2008/001188, mailed Sep. 26, 2008, 7 pages.
European Search Report for European Application No. EP 12163646, mailed Aug. 24, 2012, 5 pages.
Office Action for U.S. Appl. No. 12/820,070, mailed Feb. 20, 2013, 10 pages.
Office Action for U.S. Appl. No. 12/834,601, mailed Mar. 13, 2013, 13 pages.
International Search Report and Written Opinion for International Application No. PCT/CA2009/000808, mailed Mar. 4, 2010, 11 pages.
Office Action for U.S. Appl. No. 13/313,830, mailed Dec. 17, 2012, 22 pages.
International Search Report and Written Opinion for International Application No. PCT/CA2010/000877, mailed Oct. 20, 2010, 9 pages.
International Search Report and Written Opinion for International Application No. PCT/CA2011/050639, mailed Feb. 20, 2012, 13 pages.
International Search Report and Written Opinion for International Application No. PCT/CA2011/050755, mailed Apr. 4, 2012, 14 pages.
"DioBeam 830", pamphlet, CMS-Dental, Copenhagen, Denmark (2009), 8 pages.
"Diode laser for low level laser therapy", pamphlet, Model CTL-1106MX, Centre of Laser Technology, Laser Instruments Ltd., Warsaw, Poland (2009), 1 page.
"Hand-held therapy laser", pamphlet, Model CTL-1106MA, Centrum Techniki Laserowej, Laserinstruments Sp. zo.o, Warsaw, Poland (2009), 1 page.
"LAB pen MED LASER", pamphlet, Dr. Hinz Dental (2009), 1 page.
"Medx Phototherapy Series," pamphlet, Laser Light Canada (2006), 1 page.
"The Home Unit" pamphlet, Laser Light Canada (2009), 1 page.
"theraLASE Therapeutic Laser Treatment," pamphlet, Theralase Inc. (2009), 2 pages.
ASA Laser Therapy Company. Retrieved from the Internet: Nov. 16, 2009. <http://www.asalaser.com/uk/laser_therapy-34.html>, 2 pages.
SpectraMedics. Retrieved from the Internet: Nov. 16, 2009. <http://www.spectramedics.com/>, 3 pages.
Acumed Ltda. Retrieved from the Internet: Nov. 16, 2009. <http://www.acumed.cl/productos.php>, 10 pages.
AIIE-BEEP. Retrieved from the Internet: Dec. 8, 2009. <http://www.aiie-beep.com/index.php/en/>, 4 pages.
Apollo Physical Therapy Products LLC, Apollo 2009 Laser Products. Retrieved from the Internet: Nov. 16, 2009. <http://www.apollopt.com/products.htm>, 4 pages.
Avicenna Laser Technology, Inc. Retrieved from the Internet: Nov. 16, 2009. <http://www.avicennalaser.com/>, 1 page.
Biolase Technology, Inc.. Retrieved from the Internet: Nov. 16, 2009. <http://www.biolase.com/>, 3 pages.
CMS Dental ApS. Retrieved from the Internet: Nov. 16, 2009. <http://www.cmsdental.com/>, 2 pages.
Laserinstruments Ltd., Centre of Laser Technology. Retrieved from the Internet: Nov. 16, 2009. <http://www.ctl.com.pl/english/eindex2.html>, 1 page.
Velkommen til Easy-Laser Technology Aps, Service Division. Retrieved from the Internet: Nov. 16, 2009. <http://www.easy-laser.dk/startside.html>, 4 pages.
Erchonia. Retrieved from the Internet: Nov. 16, 2009. <http://www.erchonia.com/>, 5 pages.
GentleWaves. Retrieved from the Internet: Nov. 16, 2009. <http://www.gentlewaves.com/index.asp>, 3 pages.
GMS Green Medical Systems. Retrieved from the Internet: Nov. 16, 2009. <http://www.greenmed.co.jp/body/index-E.htm>, 2 pages.
Irradia. Retrieved from the Internet: Nov. 16, 2009. <http://www.irradia.com/>, 2 pages.
RJ-Laser, Germany. Retrieved from the Internet: Nov. 16, 2009. <http://www.rj-medical.de/>, 4 pages.
Laserex. Retrieved from the Internet: Nov. 16, 2009. <http://www.laserex.net/>, 2 pages.
Laser Therapeutics, Inc. Retrieved from the Internet: Nov. 16, 2009. <http://www.laserhealthsystems.com/>, 2 pages.
Light for Health Limited. Retrieved from the Internet: Dec. 10, 2009. <http://www.lightforhealth.co.uk/>, 1 page.
MediCom Inc. Retrieved from the Internet: Nov. 16, 2009. <http://www.medicom.cz/en/index.php>, 2 pages.
MedSolution. Retrieved from the Internet: Nov. 16, 2009. <http://www.medsolution.de/>, 3 pages.
MedX Health. Retrieved from the Internet: Nov. 16, 2009. <http://www.medxhealth.com/>, 2 pages.
Meridian Co., Ltd. Retrieved from the Internet: Nov. 16, 2009. <http://www.meridian.co.kr/>, 3 pages.
MKW Lasersysteme. Retrieved from the Internet: Nov. 16, 2009. <http://www.mkw-laser.de/MKW-Site_NEU/Sites/en/index.html>, 2 pages.
MM Optics Ltda. Retrieved from the Internet: Nov. 16, 2009. <http://www.mmo.com.br/index_eng.asp>, 4 pages.
Omega Laser Systems. Retrieved from the Internet: Nov. 16, 2009. <http://www.omegalaser.co.uk/>, 2 pages.
Petrolaser Company. Retrieved from the Internet: Nov. 16, 2009. <http://www.petrolaser.spb.ru/indexe.htm>, 2 pages.
RianCorp Pty Ltd. Retrieved from the Internet: Nov. 16, 2009. <http://www.riancorp.com/>, 3 pages.
ScalarWave Lasers. Retrieved from the Internet: Nov. 16, 2009. <http://www.scalarwavelasers.com/>, 4 pages.
SKF Services, Ltd. Retrieved from the Internet: Nov. 16, 2009. <http://www.skfservices.com/>, 3 pages.
Laseuropa Kft. Retrieved from the Internet: Nov. 16, 2009. <http://www.softlaser.hu/company.php>, 1 page.
Theralase Corporate. Retrieved from the Internet: Nov. 16, 2009. <http://www.theralase.com/>, 2 pages.
THOR Laser. Retrieved from the Internet: Nov. 16, 2009. <http://www.thorlaser.com/>, 3 pages.
Abi-Ramia, L. B. P. et al., "Effects of low-level laser therapy and orthodontic tooth movement on dental pulps in rats," Angle Orthod., 80(1):116-122 (2010).
Ad, N. et al., "Impact of low level laser irradiation on infarct size in the rat following myocardial infarction," International Journal of Cardiology, 80:109-116 (2001).
Agaiby, A. D. et al., "Laser modulation of angiogenic factor production by T-lymphocytes," Lasers Surg Med., 26(4):357-363 (2000) (Abstract).
Aihara, N. et al., "Low-energy irradiation stimulates formation of osteoclast-like cells via RANK expression in vitro," Lasers Med. Sci., 21:24-33 (2006).

(56) References Cited

OTHER PUBLICATIONS

Ajdukovic, Z. et al., "Repair of bone tissue affected by osteoporosis with hydroxyapatite-Poly-L-lactide (HAp-PLLA) with and without blood plasma," Journal of Biomaterials Applications, 20:179-190 (2005).
Akin, E. et al., "Effects of nitric oxide in orthodontic tooth movement in rats," Am. J. Orthod. Dentofacial Orthop., 126(5):608-614 (2004).
Albrecht-Buehler, G., "Changes of cell behavior by near-infrared signals," Cell Motility and the Cytoskeleton, 32:299-304 (1995).
Alexandratou, E. et al., "Human fibroblast alterations induced by low power laser irradiation at the single cell level using confocal microscopy," Photochem. Photobiol. Sci., 1:547-552 (2002).
Almeida-Lopes, L. et al., "Comparison of the low level laser therapy effects on cultured human gingival fibroblasts proliferation using different irradiance and same fluence," Lasers in Surgery and Medicine, 29(2):179-184 (2001).
Aoki, A. et al., "Lasers in nonsurgical periodontal therapy," Periodontology 2000, 36:59-97 (2004).
Barushka, O. et al., "Effect of low-energy laser (He-Ne) irradiation on the process of bone repair in the rat tibia," Bone, 16(1):47-55 (1995).
Bibikova, A. et al., "Enhancement of angiogenesis in regenerating gastrocnemius muscle of the toad (Bufo viridis) by low-energy laser irradiation," Anat. Embryol, 190(6):597-602 (1994).
Bischoff-Ferrari, H. A. et al., "Fracture prevention with vitamin D supplementation: a meta-analysis of randomized controlled trials," JAMA, 293(18):2257-2264 (2005).
Bouquot, J. et al., "Combined new technologies to improve dental implant success—quantitative ultrasound evaluation of NIR-LED photobiomodulation," Abstracts of the 2008 Annual Meeting of the American Academy of Oral Medicine, p. e6 (2008).
Bouquot, J. E. et al., "Combined new technologies to improve dental implant success and quantitative ultrasound evaluation of NIR-LED photobiomodulation," Proceedings of Light-Activated Tissue Regeneration and Therapy Conference, Waynant, R. and Tata, D.B. (eds.), Springer Science+Business Media, LLC, pp. 191-206 (2008).
Brawn, P. R. et al., "Histologic comparison of light emitting diode phototherapy-treated hydroxyapatite-grafted extraction sockets: a same-mouth case study," Implant Dentistry, 16(2):204-211 (2007).
Brawn, P. et al., "Accelerated implant stability after LED photomodulation treatment," EAO, Barcelona (2007), 2 pages.
Brudvik, P. et al., "Multi-nucleated cells remove the main hyalinized tissue and start resorption of adjacent root surfaces," Eur J Orthod., 16(4):265-273 (1994).
Brudvik, P. et al., "Root resorption beneath the main hyalinized zone," Eur J Orthod., 16(4):249-263 (1994).
Brudvik, P. et al., "The initial phase of orthodontic root resorption incident to local compression of the periodontal ligament," Eur J Orthod., 15(4):249-263 (1993).
Burcu, K-A, "The effects of Nd: YAG laser on maxillary canine distalization rate," Turkish Journal of Orthodontics, 22:16-25 (2009).
Byrnes, K. R. et al., "Light promotes regeneration and functional recovery and alters the immune response after spinal cord injury," Lasers in Surgery and Medicine, 36:171-185 (2005).
Clokie, C., et al., "The effects of the helium-neon laser on post-surgical discomfort: a pilot study," Journal of the Canadian Dental Association, 57(7):584-586 (1991).
Cobb, C. M., "Lasers in periodontics: a review of the literature," Journal of Periodontology, 77:545-564 (2006).
Collins, M. K. et al., "The local use of vitamin D to increase the rate of orthodontic tooth movement," Am J. Orthod. Dentofac. Orthop., 94:278-284 (1988).
Cruz, D. R. et al., "Effects of low-intensity laser therapy on the orthodontic movement velocity of human teeth: a preliminary study," Lasers in Surgery and Medicine, 35:117-120 (2004).
Da Silva, R. V. et al., "Repair of bone defects treated with autogenous bone graft and low-power laser," Journal of Craniofacial Surgery, 17(2):297-301 (2006).

Demir, H. et al., "Comparison of the effects of laser, ultrasound, and combined laser/ultrasound treatments in experimental tendon healing," Lasers in Surgery and Medicine, 3584-3589 (2004).
Dortbudak, O. et al., "Effect of low-power laser irradiation on bony implant sites," Clin Oral Impl. Res., 13(3):288-292 (2002).
Dortbudak, O. et al., "Biostimulation of bone marrow cells with a diode soft laser," Clinical Oral Implants Research, 11(6):540-545 (2000).
Eells, J. T. et al., "Mitochondrial signal transduction in accelerated wound and retinal healing by near-infrared light therapy," Mitochondrion, 4(5-6):559-567 (2004).
El Sayed, S. O. et al., "Effect of laser pulse repetition rate and pulse duration on mast cell number and degranulation," Lasers in Surgery and Medicine, 19:433-437 (1996).
Enwemeka, C. S., "Laser biostimulation of healing wounds: specific effects and mechanisms of action," The Journal of Orthopaedic and Sports Physical Therapy, 9(10):333-338 (1988).
Featherstone, J. D. B. et al., "Laser effects on dental hard tissues," Adv. Dent. Res., 1(1):21-26 (1987).
Frost, H. M., "Wolff's Law and bone's structural adaptations to mechanical usage: an overview for clinicians," The Angle Orthodontist, 64(3):175-188 (1994).
Fujita, S. et al., "Low-energy laser stimulates tooth movement velocity via expression of RANK and RANKL," Orthod Craniofac Res, 11:143-155 (2008).
Fujiyama, K. et al., "Clinical effect of $CO_2$ laser in reducing pain in orthodontics," Angle Orthodontist, 78(2):299-303 (2008).
Ghamsari, S. M. et al., "Evaluation of low level laser therapy on primary healing of experimentally induced full thickness teat wounds in dairy cattle," Vet Surg., 26(2):114-120 (1997) (Abstract).
Gorur, I. et al., "Low-level laser therapy effects in traumatized permanent teeth with extrusive luxation in an orthodontic patient," Angle Orthod., 80(5):968-974 (2010).
Goulart, C. S. et al., "Photoradiation and orthodontic movement: experimental study with canines," Photomedicine and Laser Surgery, 24(2):192-196 (2006).
Gruppo, R. et al., "The pathophysiology of alveolar osteonecrosis of the jaw: anticardiolipin antibodies, thrombophilia, and hypofibrinolysis", J. Lab. Clin. Med., 127(5):481-488 (1996).
Guzzardella, G. A. et al., "Laser stimulation on bone defect healing: an in vitro study," Lasers Med. Sci., 17:216-220 (2002).
Hashimoto, F. et al., "Administration of osteocalcin accelerates orthodontic tooth movement induced by a closed coil spring in rats," European Journal of Orthodontics, 23:535-545 (2001).
Hawkins, D. et al., "Effect of multiple exposures of low-levellaser therapy on the cellular responses of wounded human skin fibroblasts," Photomedicine and Laser Surgery, 24(6):705-714 (2006).
Houreld, N. N. et al., "Irradiation at 830 nm stimulates nitric oxide production and inhibits pro-inflammatory cytokines in diabetic wounded fibroblast cells," Lasers in Surgery and Medicine, 42(6):494-502 (2010).
Jiang, R.-P. et al., "Root resorption before and after orthodontic treatment: a clinical study of contributory factors," Eur J Orthod., doi:10.1093/ejo/cjpl165 (2010).
Kaipatur, N. et al., "Effect of infrared radiation on mandible condylar growth in rats," IADR General Session, Miami, FL, 1 page, (2009).
Karu, T. I. et al., "Exact action spectra for cellular responses relevant to phototherapy," Photomedicine and Laser Surgery, 23(4):355-361 (2005).
Karu, T. I. et al., "Absorption measurements of a cell monolayer relevant to phototherapy: reduction of cytochrome c oxidase under near IR radiation," Journal of Photochemistry and Photobiology B: Biology B1, 81(2):98-106 (2005).
Kau, C. H., "A radiographic analysis of tooth morphology following the use of a novel cyclical force device in orthondontics," Head & Face Medicine, 7:14 (2011), 5 pages.
Kawakami, M. et al., "Local injection of 1,25-dihydroxyvitamin $D_3$ enhanced bone formation for tooth stabilization after experimental tooth movement in rats," J Bone Miner Metab., 22(6):541-546 (2004).
Kawakami, M., "Effects of local application of 1,25 (OH)2D3 on experimental tooth movement in rats," Osaka Daigaku Shigaku Zasshi, 35(1):128-146 (1990) (English-language abstract).

(56) References Cited

OTHER PUBLICATIONS

Kawasaki, K. et al., "Effects of low-energy laser irradiation on bone remodeling during experimental tooth movement in rats," Lasers in Surgery and Medicine, 26:282-291 (2000).

Khadra, M. et al., "Effect of laser therapy on attachment, proliferation and differentiation of human osteoblast-like cells cultured in titanium implant material," Biomaterials, 26(17):3503-3509 (2005).

Khadra, M. et al., "Low-level laser therapy stimulates bone-implant interaction: an experimental study in rabbits," Clin. Oral Implants Res., 15(3):325-332 (2004).

Khadra, M. et al., "The effect of low level laser irradiation on implant-tissue interaction. In vivo and in vitro studies," Swed. Dent. J. Suppl., 172:1-63 (2005) (Abstract).

Khadra, M. et al., "Determining optimal dose of laser therapy for attachment and proliferation of human oral fibroblasts cultured on titanium implant material," Journal of Biomedical Materials Research, 73A(1):55-62 (2005).

Khadra, M. et al., "Enhancement of bone formation in rat calvarial bond defects using low-level laser therapy," Oral Surg. Oral Med. Oral Pathol. Oral Radial. Endod., 97:693-700 (2004).

Khadra, M. et al., "Laser therapy accelerates initial attachment and subsequent behaviour of human oral fibroblasts cultured on titanium implant material: a scanning electron microscopic and histommphometric analysis," Clin. Oral Impl. Res., 16:168-175 (2005).

Kim, S-J et al., "Effects of low-level laser therapy after corticision on tooth movement and paradental remodlling," Lasers in Surgery and Medicine, 41:524-533 (2009).

Kim, Y-D et al., "Low-level laser irradiation facilitates fibronectin and collagen type I turnover during tooth movement in rats," Lasers Med. Sci., Springer-Verlag London Ltd. (2008).

Kreisler, M. et al., "Effect of low-level GaAIAs laser irradiation on the proliferation rate of human periodontal ligament fibroblasts: an in vitro study," J Clin Periodontol, 30(4):353-358 (2003) (Abstract).

Kreisler, M. et al., "Low level 809-nm diode laser-induced in vitro stimulation of the proliferation of human gingival fibroblasts," Lasers in Surgery and Medicine, 30(5):365-369 (2002).

Kucerova, H. et al., "Low-level laser therapy after molar extraction," Journal of Clinical Laser Medicine & Surgery, 18(6):309-315 (2000).

Kujawa, J. et al., "Effect of low-intensity (3.75-25 J/cm$^2$) near-infrared (810 nm) laser radiation on red blood cell ATPase activities and membrane structure," Journal of Clinical Laser Medicine & Surgery, 22(2):111-117 (2004).

Kvam, E., "Scanning electron microscopy of tissue changes on the pressure surface of human premolars following tooth movement," Scand. J. Dent. Res., 80(5):357-368 (1972).

Kwong-Hing, A. et al., "Accelerated implant stability in indirect sinus lifts with bone grafts using LED phototherapy," Shenzhen (2006), 1 page.

Lim, H-M et al., "A clinical investigation of the efficacy of low level laser therapy in reducing orthodontic postadjustment pain," Am. J. Orthod. Dentofacial Orthop., 108:614-622 (1995).

Limpanichkul, W. et al., "Effects of low-level laser therapy on the rate of orthodontic tooth movement," Orthod. Craniofacial Res., 9:38-43 (2006).

Lopes, C. B. et al., "Infrared laser light reduces loading time of dental implants: a Raman spectroscopic study," Photomedicine and Laser Surgery, 23(1):27-31 (2005).

Luger, E. J. et al. "Effect of low-power laser irradiation on the mechanical properties of bone fracture healing in rats," Lasers in Surgery and Medicine, 22(2):97-102 (1998).

Maegawa, Y. et al., "Effects of near-infrared low-level laser irradiation on microcirculation," Lasers in Surgery and Medicine, 27(5):427-437 (2000).

Marques, M. M. et al., "Effect of low-power laser irradiation on protein synthesis and ultrastructure of human gingival fibroblasts," Lasers in Surgery and Medicine, 34:260-265 (2004).

Mathews, D. P. et al., "Managing treatment for the orthodontic patients with periodontal problems," Seminars in Orthodontics, 3(1):21-38 (1997).

Meguro, D. et al., "Laser irradiation inhibition of open gingival embrasure space after orthodontic treatment," Aust Orthod J., 18(1):53-63 (2002).

Melsen, B., "Tissue reaction to orthodontic tooth movement—a new paradigm," Eur J Orthod., 23(6):671-681 (2001).

Mendez, T. M. et al., "Dose and wavelength of laser light have influence on the repair of cutaneous wounds," J Clin Laser Med Surg, 22(1):19-25 (2004) (Abstract).

Merli, L., "Effect of low-intensity laser irradiation on the process of bone repair," Photomedicine and Laser Surgery, 23(2):212-215 (2005).

Moriyama, E. H. et al., "Dentin evaluation after Nd: YAG laser irradiation using short and long pulses," Journal of Clinical Laser Medicine & Surgery, 22(1):43-50 (2004).

Moriyama, Y. et al., "In vivo effects of low level laser therapy on inducible nitric oxide synthase," Lasers in Surgery and Medicine, 41(3):227-231 (2009).

Nicolau, R. A. et al., "Effect of low-power GaAIAs laser (660 nm) on bone structure and cell activity: an experimental animal study," Lasers Med. Sci., 18(2):89-94 (2003).

Ninomiya, T. et al., "High-intensity pulsed laser irradiation accelerates bone formation in metaphyseal trabecular bone in rat femur," J. Bone Miner Metab., 21(2):67-73 (2003).

Ninomiya, T. et al., "Increase of bone volume by a nanosecond pulsed laser irradiation is caused by a decreased osteoclast number and an activated osteoblasts," Bone, 40:140-148 (2007).

Nissan, J. et al., "Effect of low intensity laser irradiation on surgically created bony defects in rats," Journal of Oral Rehabilitation, 33:619-624 (2006).

Ontiveros, J. C. et al., "Clinical evaluation of a chairside whitening lamp and bleaching efficacy," #1081, The University of Texas, Dental Branch at Houston (2008). Retrieved from the Internet on Oct. 14, 2009. <http://www.discusdental.com/files/University%20of%/20Texas.pdf>, 1 page.

Oron, U. et al., "Ga-As (808 nm) laser irradiation enhances ATP production in human neuronal cells in culture," Photomedicine and Laser Surgery, 25(3):180-182 (2007).

Owman-Moll, P. et al., "The effects of a four-fold increased orthodontic force magnitude on tooth movement and root resorptions. An intra-individual study in adolescents," Eur J Orthod., 18(3):287-94 (1996).

Ozawa, Y. et al., "Low-energy laser irradiation stimulates bone nodule formation at early stages of cell culture in rat calvarial cells," Bone, 22(4):347-354 (1998) (Abstract).

Ozkan, N. et al., "Investigation of the supplementary effect of GaAs laser therapy on the rehabilitation of human digital flexor tendons," Journal of Clinical Laser Medicine & Surgery, 22(2):105-110 (2004).

Paetyangkul, A. et al., "Physical properties of root cementum: Part 14. The amount of root resorption after force application for 12 weeks on maxillary and mandibular premolars: a microcomputed-tomography study," Am J Orthod Dentofacial Orthop., 136(4):492.e1-492.e9 (2009).

Pereira, A. N. et al., "Effect of low-power laser irradiation on cell growth and procollagen synthesis of cultured fibroblasts," Lasers in Surgery and Medicine, 31(4):263-267 (2002).

Pinheiro, A. L. et al., "Effect of 830-nm laser light on the repair of bone defects grafted with inorganic bovine bone and decalcified cortical osseus membrane," J Clin Laser Med Surg., 21(5):301-306 (2003) (Abstract).

Pinheiro, A. L. B. et al., "Photoengineering of bone repair processes," Photomedicine and Laser Surgery, 24(2):169-178 (2006).

Pourzarandian, A. et al., "Effect of low-level Er: YAG laser irradiation on cultured human gingival fibroblasts," J. Periodontal, 76:187-193 (2005).

Raghoebar, G. M. et al., "Does platelet-rich plasma promote remodeling of autologous bone grafts used for augmentation of the maxillary sinus floor?," Clin. Oral Impl. Res., 16:349-356 (2005).

Ren, Y. et al., "The rat as a model for orthodontic tooth movement—a critical review and a proposed solution," European Journal of Orthodontics, 26(5):483-490 (2004).

Renno, A. C. M. et al., "Effects of 830-nm Laser, used in two doses, on biomechanical properties of osteopenic rat femora," Photomedicine and Laser Surgery, 24(2):202-206 (2006).

(56) References Cited

OTHER PUBLICATIONS

Renno, A. C. M. et al., "The effects of infrared-830 nm laser on exercised osteopenic rats," Lasers Med. Sci., 21:202-207 (2006).
Rygh, P., "Ultrastructural cellular reactions in pressure zones of rat molar periodontium incident to orthodontic tooth movement," Acta Odontol Scand., 30(5):575-593 (1972).
Rygh, P., "Ultrastructural vascular changes in pressure zones of rat molar periodontium incident to orthodontic movement," Scand J Dent Res., 80(4):307-321 (1972).
Saito, S. et al., "Stimulatory effects of low-power laser irradiation on bone regeneration in rnidpalatal suture during expansion in the rat," Am J. Orthod. Dentofac. Orthop., 111:525-532 (1997).
Samoilova, K. A. et al., "Role of Nitric Oxide in the Visible Light-Induced Rapid Increase of Human Skin Microcirculation at the Local and Systemic Level: I. Diabetic Patients," Photomedicine and Laser Surgery, 26(5):433-442 (2008).
Samoilova, K. A. et al., "Role of Nitric Oxide in the Visible Light-Induced Rapid Increase of Human Skin Microcirculation at the Local and Systemic Levels: II. Healthy Volunteers," Photomedicine and Laser Surgery, 26(5):443-449 (2008).
Schindl, A. et al., "Direct stimulatory effect of low-intensity 670 nm laser irradiation on human endothelial cell proliferation," Br J Dermatol, 148(2):334-336 (2003) (Abstract).
Scott, P. et al., "Alignment efficiency of Damon3 self-ligating and conventional orthodontic bracket systems: a randomized clinical trial," American Journal of Orthodontics and Dentofacial Orthopedics, 134:470.e1 -470.e8 (2008).
Sebaoun, J-D. et al., "Modeling of trabecular bone and lamina dura following selective alveolar decortication in rats," J. Periodontol., 79(9):1679-1688 (2008).
Seifi, M. et al., "Effects of two types of low-level laser wave lengths (850 and 630 nm) on the orthodontic tooth movements in rabbits," Lasers Med. Sci., 22:261-264 (2007).
Seifi, M. et al., "The effect of 904 nm low level laser on condylar growth in rats," Laser Med Sci, 25:61-65 (2010).
Shankland, W. E., et al., "Medullary and odontogenic disease in the painful jaw: clinicopathologic review of 500 consecutive lesions," Journal of Craniomandibular Practice, 20(4):295-303 (2002).
Shimotoyodome, A. et al., "Improvement of macromolecular clearance via lymph flow in hamster gingiva by low-power carbon dioxide laser-irradiation," Lasers in Surgery and Medicine, 29:442-447 (2001).
Shirazi, M. et al., "The role of nitric oxide in orthodontic tooth movement in rats," Angle Orthod., 72(3):211-215 (2002).
Silva, A. N. et al., "Computerized morphometric assessment of the effect of low-level laser therapy on bone repair: an experimental animal study," Journal of Clinical Laser Medicine & Surgery, 20(2):83-87 (2002).
Sousa, M., "Influence of low-intensity laser on the rate of orthodontic movement," http://ibict.metodista.br/tedeSimplificado/tde_busca/arquivo.php?codArquivo=1145 (2008) (English Abstract).
Sousa, M. et al., "Influence of low-level laser on the speed of orthodontic movement," Photomedicine and Laser Surgery, 29(3):191-196 (2011).
Stadler, I. et al., "In vitro effects of low-level laser irradiation of 660 nm on peripheral blood lymphocytes," Lasers in Surgery and Medicine, 27(3):255-261 (2000).
Stein, A. et al., "Low-level laser irradiation promotes proliferation and differentiation of human osteoblasts in vitro," Photomedicine and Laser Surgery, 23(2):161-166 (2005).
Stephens, B. J., "How much 'useful' radiation does the sun deliver? Very Expensive Sunlight," Laser Therapy Products LLC (d/b/a K-Laser), K-Laser USA, URL: <http://www.k-laserusa.com/how-much-useful-radiation-does-the-sun-deliver/(retrieved on Dec. 7, 2012)>, (2012), 3 pages.
Sun, X. et al., "Effects of low energy laser on tooth movement and remodeling of alveolar bone in rabbits," School of Stomatology, Jilin University, 19(5):290-293 (2001) (English Abstract).

Takano-Yamamoto, T. et al., "Effect of age on the rate of tooth movement in combination with local use of $1,25(OH)_2$ $D_3$ and mechanical force in the rat," J. Dent. Res., 71:1487-1492 (1992).
Takano-Yamamoto, T. et al., "The effect of local application of 1,25-Dihydroxycholecalciferol on osteoclast numbers in orthodontically treated rats," J. Dent. Res., 71:53-59 (1992).
Takeda, Y., "Irradiation effect of low energy laser on alveolar bone after tooth extraction: experimental study in rats," International Journal of Oral Maxillofacial Surgery, 17:388-391 (1988).
Trelles, M. A. et al., "Red light-emitting diode (LED) therapy accelerates wound healing post-blepharoplasty and periocular laser ablative resurfacing," Journal of Cosmetic and Laser Therapy, 8:39-42 (2006).
Turhani, D. et al., "Pain relief by single low-level laser irradiation in orthodontic patients undergoing fixed appliance therapy," Am J Orthod Dentofacial Orthop., 130(3):371-377 (2006).
Ueda, Y. et al., "Effects of pulse frequency of low-level laser therapy (LLLT) on bone nodule formation in rat calvarial cells," J Clin Laser Med Surg., 21(5):271-277 (2003) (Abstract).
Ueda, Y. et al., "Pulse irradiation of low-power laser stimulates bone nodule formation," J Oral Sci., 43(1):55-60 (2001) (Abstract).
Uysal, T. et al., "Resonance frequency analysis of orthodontic miniscrews subjected to light-emitting diode photobiomodulation therapy," Eur J Orthod., pp. 1-8, dot 10.1093/ejo/cjq166 (2010).
Verna, C. et al., "The rate and the type of orthodontic tooth movement is influenced by bone turnover in a rat model," European Journal of Orthodontics, 22(4):343-352 (2000).
Vinck, E. M. et al., "Increased fibroblast proliferation induced by light emitting diode and low power laser irradiation," Lasers Med. Sci., 18:95-99 (2003).
Wahab, R. M. A. et al., "Comparison of self- and conventional-ligating brackets in the alignment stage," European Journal of Orthodontics, doi:10.1093/ejo/cjq179 (2011).
Walsh, L. J., "The current status of low level laser therapy in dentistry. Part 2. Hard tissue applications," Australian Dental Journal, 42(5):302-306 (1997).
Waynant, R. W. et al. (eds.), "Proceedings of Light Activated Tissue Regeneration and Therapy Conference," Lecture Notes in Electrical Engineering, Springer (2008), 32 pages.
Weber, J. B. B. et al., "Laser therapy improves healing of bone defects submitted to autologus bone graft," Photomedicine and Laser Surgery, 24(1):38-44 (2006).
Weltman, B. et al., "Root resorption associated with orthodontic tooth movement: a systematic review," Am J Orthod Dentofacial Orthop., 137(4):462-476 (2010).
Whelan, H. T. et al., "Effect of NASA light-emitting diode irradiation on wound healing," Journal of Clinical Laser Medicine & Surgery, 19(6):305-314 (2001).
Wong-Riley, M. T. et al., "Photobiomodulation directly benefits primary neurons functionally inactivated by toxins: role of cytochrome c oxidase", The Journal of Biological Chemistry, 280(6):4761-4771 (2005).
Wong-Riley, M. T. et al., "Light-emitting diode treatment reverses the effect of TTX on cytochrome oxidase in neurons", NeuroReport, 12(14):3033-3037 (2001).
Yaakobi, T. et al., "Promotion of bone repair in the cortical bone of the tibia in rats by low energy laser (He-Ne) irradiation," Calcif Tissue Int., 59(4):297-300 (1996) (Abstract).
Yamaguchi, M. et al., "Low-energy laser irradiation stimulates the tooth movement velocity via expression of M-CSF and c-fms," Orthodontic Waves, 66:139-148 (2007).
Yamasaki, K. et al., "Prostaglandin as a mediator of bone resorption induced by experimental tooth movement in rats," J. Dent. Res., 59(10):1635-1642 (1980).
Ying, R. et al., "Pretreatment with near-infrared light via light-emitting diode provides added benefit against rotenone- and MPP+ -induced neurotoxicity," Brain Research, 1243:167-173 (2008).
Youssef, M. et al., "The effect of low-level laser therapy during orthodontic movement: a preliminary study," Lasers Med. Sci., 23(1):27-33 (2008).
Yoshida, T. et al., "Low-energy laser irradiation accelerates the velocity of tooth movement via stimulation of the alveolar bone remodeling," Orthodontics & Craniofacial Research, 12:289-298 (2009).

(56) References Cited

OTHER PUBLICATIONS

Zhu, X. et al., "A study on expression of basic fibroblast growth factors in periodontal tissue following orthodontic tooth movement associated with low power laser irradiation," Department of Orthodontics, School for Stomatology, Jilin University, 20(3):166-168 (2002) (English Abstract).
Supplementary European Search Report for European Application No. 08772845, mailed Mar. 21, 2014, 7 pages.
Office Action for U.S. Appl. No. 12/820,070, mailed Jan. 29, 2014, 11 pages.
Office Action for U.S. Appl. No. 13/895,327, mailed Feb. 4, 2014, 5 pages.
Supplementary European Search Report for European Application No. 11831892, mailed Mar. 4, 2014, 6 pages.
Office Action for U.S. Appl. No. 13/826,383, mailed Mar. 26, 2014, 11 pages.
Office Action for U.S. Appl. No. 13/314,006, mailed Jul. 8, 2014, 25 pages.
Third-Party Submission Under 37 CFR 1.290 for U.S. Appl. No. 13/866,831, filed on Apr. 23, 2014, 48 pages.
Bakr, A. et al., "Osteogenesis in the glenoid fossa in response to mandibular advancement," American Journal of Orthodontics and Dentofacial Orthopedics, 119(4):390-400 (2001).
Eells, J. T. et al., "Therapeutic photobiomodulation for methanol-induced retinal toxicity," PNAS, 100(6):3439-3444 (2003).
Hashimoto, H., "Effect of micro-pulsed electricity on experimental tooth movement," The Journal of Japan Orthodontic Society, 49(4):352-361 (1990).
Kau, C. H., Biotechnology in Orthodontics, Dentistry, 2(5):e108 (2012).
Kau, C. H., "Orthodontics in the 21st century: a view from across the pond," J Orthod., 39(2):75-76 (2012).
Nishimura, M. et al., "Periodontal tissue activation by vibration: intermittent stimulation by resonance vibration accelerates experimental tooth movement in rats," Am J Orthod Dentofacial Orthop., 133(4):572-583 (2008).
Pancherz, H. et al., "Dentofacial orthopedics in relation to somatic maturation: An analysis of 70 consecutive cases treated with the Herbst appliance," American Journal of Orthodontics, 88(4):273-287 (1985).
Pancherz, H. et al., "Amount and direction of temporomandibular joint growth changes in Herbst treatment: a cephalometric long-term investigation," Angle Orthod., 73(5):493-501 (2003).
Proffit, W. R. et al., Excerpts from Chapters 14-17 In: Contemporary Orthodontics, Fourth Edition, Mosby-Elsevier 2007, pp. 551, 577, 602 and 617, 8 pages.
Ruf, S. et al., "Temporomandibular joint growth adaptation in Herbst treatment: a prospective magnetic resonance imaging and cephalometric roentgenographic study," European Journal of Orthodontics, 20:375-388 (1998).
Tuby, H. et al., "Low-level laser irradiation (LLLI) promotes proliferation of mesenchymal and cardiac stem cells in culture," Lasers Surg Med., 39(4):373-378 (2007).
Wiechmann, D. et al., "Control of mandibular incisors with the combined Herbst and completely customized lingual appliance—a pilot study," Head & Face Medicine, 6:3 (2010), 4 pages.
Supplementary European Search Report for European Application No. 11846346.2, mailed Jun. 17, 2014, 5 pages.

LIGHT THERAPY APPARATUS AND METHODS

REFERENCE TO RELATED APPLICATION

This application is a continuation of U.S. patent application Ser. No. 11/767,302, filed on Jun. 22, 2007, now abandoned, which is a continuation-in-part of U.S. patent application Ser. No. 11/355,583, filed on Feb. 16, 2006, now abandoned, which claims the benefit of U.S. provisional application No. 60/705,753, filed on Aug. 5, 2005 and U.S. provisional application No. 60/653,828, filed on Feb. 17, 2005.

TECHNICAL FIELD

This invention relates to light therapy. Apparatus and methods according to the invention may be applied to the treatment of bone disorders and the biostimulation of bone and soft tissue. Embodiments of the invention provide apparatus for irradiating tissues of the face and jaw with biologically effective doses of light.

BACKGROUND

Light therapy involves irradiating tissues with light. Light can stimulate a variety of biological activities in cells and tissues that are compromised in function. Light therapy treatment is typically administered by a physician or therapist who directs light from a hand-held light emitting device at an affected area. Light emitting devices can be difficult to position consistently over the affected area. Sometimes a tattoo is used to identify the affected area. However, even with a tattoo or other reference mark it is difficult to consistently deliver light therapy treatments to an affected area.

Light therapy typically involves repeated treatments over at least several days. Thus, patients undergoing light therapy may be required to make multiple visits to a practitioner's office or clinic in order to complete a therapy regimen. Such repeated visits may be time consuming and/or expensive.

LEDs and other light sources suitable for generating light for light therapy can get hot when they operate. Such light sources can be inefficient at higher temperatures. Hot apparatus can also be uncomfortable or even dangerous to patients.

The inventor has identified a need or desire for light therapy apparatus which can deliver consistent treatments, particularly to tissues in the dental and maxillofacial areas. There is a particular need or desire for such apparatus that is sufficiently cost-effective and foolproof to be used at home by patients. There is also a need for such apparatus that can be operated without exposing a patient to high temperature surfaces.

SUMMARY

One aspect of this invention provides apparatus for delivering light to tissues of a patient's dental and maxillofacial areas. The apparatus comprises a support that registers against one or more anatomical features of a patient's head and one or more light sources mounted to the support. The light sources illuminate selected tissues of a patient's dental and maxillofacial areas from outside of the patient's mouth. The light sources comprise arrays of LEDs in some embodiments.

In some embodiments the support comprises an intra-oral tray connected to an extra-oral bridge. A light source, such as a light emitting diode ("LED") array, is mounted to the extra-oral bridge.

In some embodiments, the support comprises a head-set that registers on the bridge of a patient's nose and the patient's ears. A light source, such as a light emitting diode ("LED") array, is mounted to the head-set.

Other aspects of the invention provide methods for preparing light therapy apparatus and methods for delivering light therapy.

Further aspects of the invention and features of various example embodiments of the invention are described below and/or shown in the accompanying drawings.

BRIEF DESCRIPTION OF DRAWINGS

The appended drawings illustrate non-limiting example embodiments of the invention.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
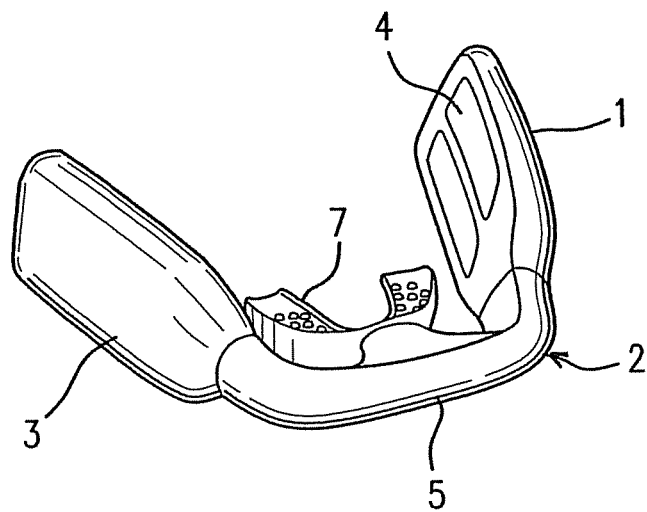
FIG. 1 is a view from the front side of an extra-oral light therapy device having an intra-oral tray, an extra-oral bridge, and left and right side extra-oral LED arrays.
Figure 2:
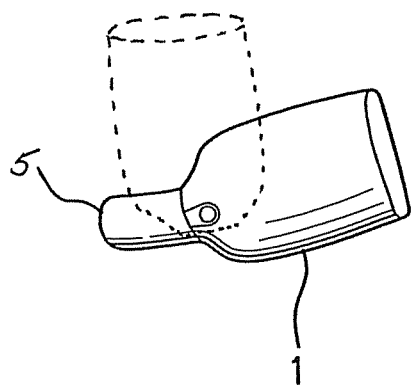
FIG. 2 is a right side view of the device of FIG. 1 with the end of the extra-oral bridge attached to the extra-oral LED array.

FIG. 1 shows an example light therapy apparatus 2 that comprises an extra-oral light source 4 having a right side 1 and a left side 3 (as viewed from the front of the device), an extra-oral bridge 5, and an intra-oral tray 7. Intra-oral tray 7 registers to a patient's teeth. Light source 4 is rigidly connected to intra-oral tray 7 by extra-oral bridge 5. Therefore, a patient can position light source 4 accurately and repeatedly to illuminate a desired location in the patient's dental and maxillofacial areas by inserting intra-oral tray 7 into his or her mouth and biting intra-oral tray 7 so that it registers to at least some of the patient's teeth. This stabilizes light therapy apparatus 2 and positions light source 4 at a desired position. The consistent alignment and targeting of light from light source 4 during subsequent treatments makes the treatments more repeatable.

Figure 3:
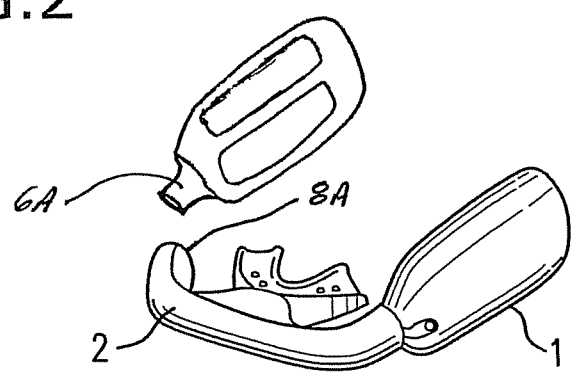
FIG. 3 is a view from the front-left side of the extra-oral bridge, intra-oral tray and extra-oral LED array of FIG. 1.

In the illustrated embodiment, extra-oral bridge 5 is removable from extra-oral light source 4 and intra-oral tray 7. Providing a light therapy apparatus 2 having major components that are detachably connectable to one another adds versatility. A design which permits the major components of the light therapy apparatus to be disassembled and reassembled while preserving alignment of extra-oral light source 4 to intra-oral tray 7 has the advantage that the apparatus can be disassembled for storage or transportation and then used immediately after assembly. FIG. 3 shows light therapy apparatus 2 with extra-oral light source left side 3 detached from extra-oral bridge 5.

Extra-oral bridge 5, extra-oral light source right side 1, and extra-oral light source left side 3 may be secured together via a suitable connector. For example, extra-oral bridge 5, the extra-oral light source right side 1, and the extra-oral light source left side 3 may be connected by inserting male connector portions 6A of the extra-oral light source right and left sides 1 and 3 into corresponding female connector portions 8A of extra-oral bridge 5 (see FIG. 3). Suitably, the suitable connector allows extra-oral light source right and left sides 1 and 3 to be detached from extra-oral bridge 5 for ease of use and flexibility.

In some embodiments, extra-oral light source right and left sides 1 and 3 are rotatable between a sagittal orientation (as shown in FIG. 1) and a vertical orientation (indicated in dotted outline in FIG. 1). Light source right and left sides 1 and 3 can be locked at a desired angle of rotation by any suitable mechanism. This permits light source right and left sides 1 and 3 to be arranged so that the light that they emit fully covers the desired treatment areas.

Figure 5:
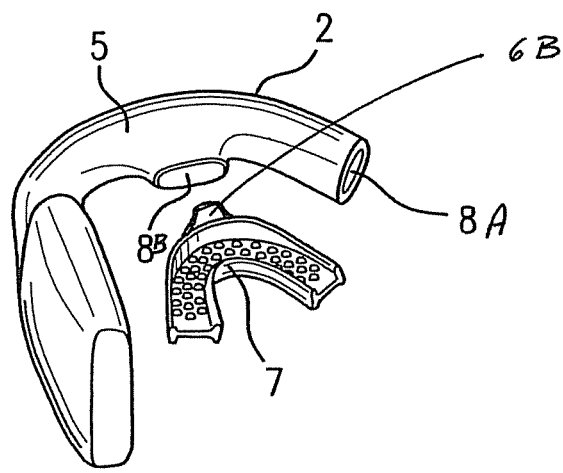
FIG. 5 is a view from the left rear side of the extra-oral bridge, intra-oral tray and extra-oral LED array of FIG. 1 with the intra-oral tray detached.

Intra-oral tray 7 may be connected to extra-oral bridge 5 by way of another suitable connector. In the embodiment illustrated in FIG. 5, a male portion 6B of intra-oral tray 7 is removably received in a female portion 8B of extra-oral bridge 5. Where intra-oral tray 7 is removable from extra-oral bridge 5, extra-oral bridge 5 may be reused for other patients (after suitable sterilization). Intra-oral tray 7 may be disposed of after it is no longer required by a patient. In some embodiments, extra-oral bridge 5 is non-removably attached to intra-oral tray 7.

Intra-oral tray 7 is intended for insertion into a patient's mouth and is suitably shaped to fit around a patient's teeth. Intra-oral tray 7 may register with a few selected teeth (for example, intra-oral tray 7 may comprise a bite tab) or may fit around the patient's full set of teeth. In one embodiment, the intra-oral tray 7 comprises a frame of a plastic or other suitable material that can serve as a skeleton for a settable material. The frame may be perforated to aid retention of the settable material. The frame may comprise extra-oral bridge 5 or a connector to connect to extra-oral bridge 5.

Prior to being used in the delivery of light therapy, the frame for intra-oral tray 7 may be filled with a suitable settable material (for example a clear vinyl siloxane gel or similar material) which sets around the patient's teeth and subsequently allows repeatable alignment of intra-oral tray 7 in the patient's mouth. Where intra-oral tray 7 could be in the path of light as it travels from light source 4 to target tissues, the material of intra-oral tray 7 should be transparent to the light.

Extra-oral bridge 5 preferably conforms around the jaw line of a patient. The light source right and left sides 1 and 3 are respectively positioned on the right and left sides of a patient's face along the patient's jaw line. Extra-oral bridge 5 may be adjustable to permit alignment of light source left and right sides 1 and 3 with target areas to be irradiated. Light source left and right sides 1 and 3 are extra-oral (outside of the patient's oral cavity). Light can pass from left and right sides 1 and 3 through tissues of the patient's lips and cheeks into target areas on the patient's gums and/or in the patient's jaws.

Figure 4:
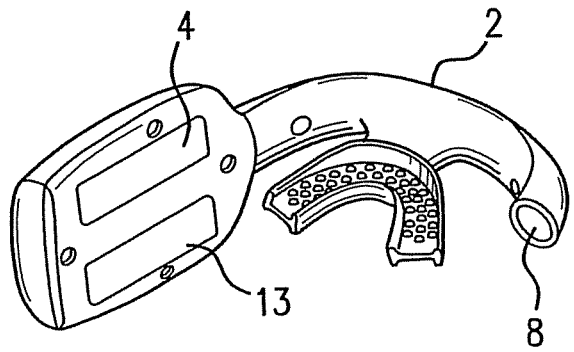
FIG. 4 is a view from the rear right side of the extra-oral bridge, intra-oral tray and extra-oral LED array of FIG. 1.

Light source 4 emits light toward the patient. The light is not necessarily visible light. For example, the light may include or consist of infrared light. Light source 4 comprises an array of light-emitting diodes (LEDs) in some embodiments. Light source 4 has an inner surface 13 (see FIG. 4) that is placed near or against the patient's skin adjacent to the tissues that it is desired to treat. Light is emitted is from inner surface 13 toward the area of treatment. In some embodiments, left and right sides 1 and 3 of light source 4 each have a length similar to a significant fraction of the length of a human jaw. For example, left and right sides 1 and 3 may each have a length of about 20 mm to about 90 mm in some embodiments and about 25 to about 45 or 60 mm in some embodiments. In cases where a light source 4 is intended to treat a localized condition, then light source 4 may be smaller in extent. In some embodiments, light source 4 has optics that emit light in the form of diverging beams. In such cases, light source 4 may be somewhat smaller than the area of tissues to be treated because light from light source 4 will spread somewhat as it passes through the tissues of the patient's lips and cheeks before reaching the tissues of the jaw and or gums to be treated.

Light source 4 may be wide enough to illuminate both upper and lower jaws of a patient simultaneously although in some embodiments light source 4 may be narrower. For example, light source 4 has a width in the range of 12 mm to about 40 mm in some embodiments (e.g. about 15 to 17 mm in some embodiments).

In some embodiments, the light is emitted by arrays of discrete LEDs. The LEDs may be arranged in any of a wide variety of patterns. For example, the LEDs may be arranged in staggered parallel rows to maximize the density of LEDs in the LED array. The LEDs may be arranged to achieve substantially uniform optical intensity over the light-emitting inner surface 13 of light source 4. In some embodiments, each array comprises 50 to 100 LEDs or other light emitters.

It is desirable that the average light intensity produced by light source 4 is at least about 10 mW/cm$^2$. In some embodiments, light source 4 has an average intensity that is, or can be adjusted to be, in the range of 20 mW/cm$^2$ to about 60 mW/cm$^2$. In some embodiments the output of light source 4 is pulsed. In such embodiments, the peak light intensity may be significantly higher than 50 mW/cm$^2$.

In some embodiments right light source 4 or its components are flexible so that they can be bent in one or two dimensions (i.e. molded) to conform to the contours of the patient's face. For example, light source 4 may comprise an array of light emitters mounted to a flexible sheet of material that will hold a shape when it is bent. The flexible material can advantageously comprise a metal sheet that can serve as a heat sink or as a thermal path to a heat sink for heat generated by the light emitters. The flexible sheet may be molded to conform to the contours of the patient's face while light therapy apparatus 2 is being fitted.

Figure 11:
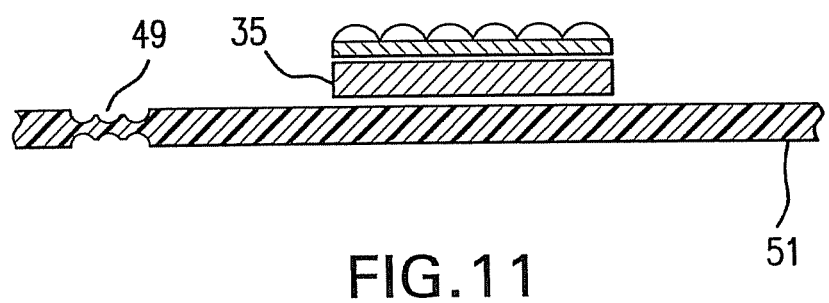
FIG. 11 is a cross-sectional view of an LED array mounted onto a substrate.
Figure 11A:
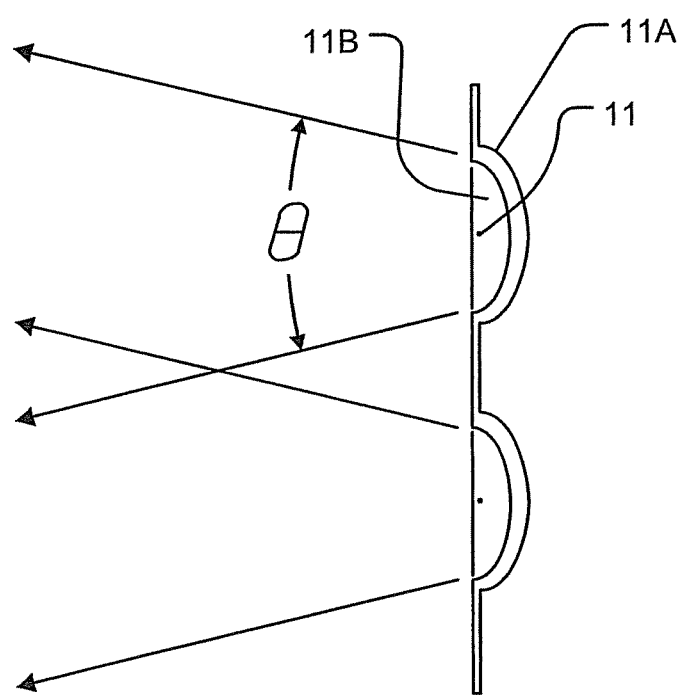
FIG. 11A is a schematic cross section through a portion of a light source having a light emitter and a reflector.

Light source 4 may include optical elements such as lenses and reflectors to focus and direct light from light source 4 onto a target area. Such optical elements may be suitably encapsulated in plastic or similar material. FIG. 11A shows a portion of a light source 4. A light emitter 11 (which may, for example, comprise a junction in a light-emitting diode or other light-emitting semiconductor device) is located adjacent to a reflective backing 11A. A curved light-reflecting recess 11B is provided adjacent to light emitter 11. Light from light source 11 is reflected in recess 11B to form a beam. The beams from all light emitters of light source 4 combine to illuminate the target tissues. The area covered by the beam will depend upon the tissues which it is desired to treat. In some embodiments, the beams of light emitted by light source 4 diverges to cover an area of tissue larger than the area of the light-emitting part of light source 4. In other embodiments the emitted light converges to provided increased light intensity at the location of the tissues that it is desired to treat. In some embodiments, the emitted light diverges in a beam having an included angle θ in the range of about 45-60°.

Since LEDs and other light emitters give off heat when they are operated, it is desirable to provide a suitable mechanism for dissipating the heat to prevent any parts of light therapy apparatus 2 that could come into contact with a patient's skin from getting too hot. For example, light source 4 may comprise a system for forced air or liquid cooling. A cooling system allows for treatment without the danger of potential burns to the patient and allows for greater efficiency and control of the device.

Figure 1A:
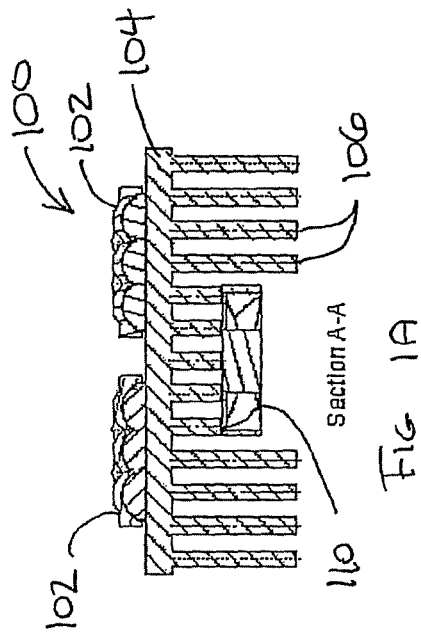
FIGS. 1A, 1B and 1C are respectively a cross-section, a front side elevation and a rear elevation of a light source having a cooling fan, a heat sink and two arrays of light emitters.
Figure 1B:
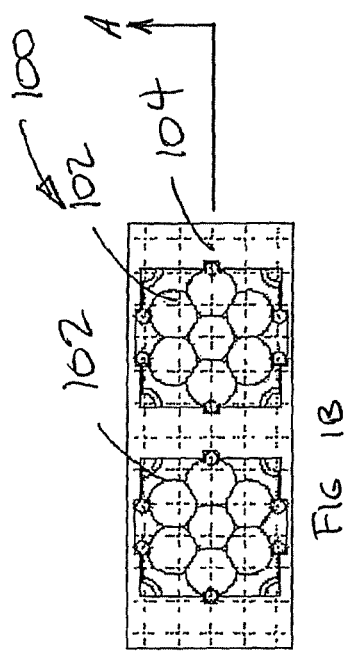
Figure 1C:
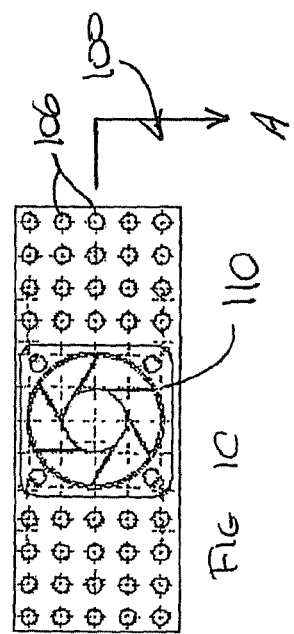

Extra-oral light source right and left sides 1 and 3 may comprise thermally-conductive LED wafers mounted on a suitable heat sink. Heat from the LED wafers is conducted into the heat sink and dissipated. FIGS. 1A, 1B and 1C show a light source 100 of a type that may be used as light source right and left sides 1 and 3. Light source 100 comprises arrays 102 of LEDs that are mounted to a heat sink 104. Heat sink 104 has pins 106 projecting from its face that is away from LED arrays 102. A fan 110 causes air to flow past pins 106 to carry away excess heat.

To be most effective, the light from light source 4 at the tissues to be treated should have at least a threshold intensity. Light source 4 may be operated in a pulsed mode to facilitate cooling of light source 4 while ensuring that when light source 4 is emitting light, the intensity of emitted light at the tissues to be treated is sufficient to be effective. In some embodiments, the duty cycle of light source 4 is 1:1 or less, in some embodiments 1:2 or less (for each interval in which light source 4 is on, light source 4 is off for two equal intervals). The pulsing of light source 4 may be performed fast enough that light source 4 does not visibly flicker (e.g. at 25 Hz or more) although this is not mandatory.

While the invention is described herein as usefully employing LEDs, other light sources such as lasers could suitably be employed. The character of the light emitted by light source right and left sides 1 and 3 will depend upon the nature of the LEDs or other light emitters in light source 4. It is generally desirable that the emitted light include light in the wavelength range of 620 nm to 1000 nm. In some embodiments the emitted light includes light having a wavelength in at least one of the following wavelength ranges: about 820 to about 890 nm and about 620 to about 680 nm. Light having wavelengths corresponding to one or more of the following ranges may be particularly effective:

613 nm to 624 nm
667 nm to 684 nm
750 nm to 773 nm
812 nm to 846 nm.

The range 613 nm to 624 nm corresponds to a band at which reduced cytochrome c oxidase absorbs light. The range 812 nm to 846 nm corresponds to a band at which oxidized cytochrome c oxidase absorbs light.

The light is substantially monochrome in some embodiments although this is not mandatory. Providing light emitters that emit at multiple wavelengths allows for irradiation over multiple wavelengths for greater biological activity. The light may comprise incoherent light although this is not mandatory. The light may be delivered continuously or pulsed at suitable frequencies and duty cycles.

Invisible infrared light can be clinically effective. In some embodiments in which the emitted light includes infrared light, the emitted light also includes bright visible light. The bright visible light deters users from looking into the light source when it is operating, provides a perceptible indication that the apparatus is operating, and may be useful in properly positioning the device. The visible light may be, but is not necessarily in a wavelength range that is beneficial for light therapy. In some embodiments, the ratio of the intensities of the visible and infrared components of the light is 1 part or less visible light to 5 parts or more infrared light.

The treatment area and desired light characteristics will vary from patient to patient. A physician, dentist or other therapist can determine a light treatment regime for a patient and set up light therapy apparatus 2 to operate light emitters in light source 4 to provide the desired treatment.

Figure 6:
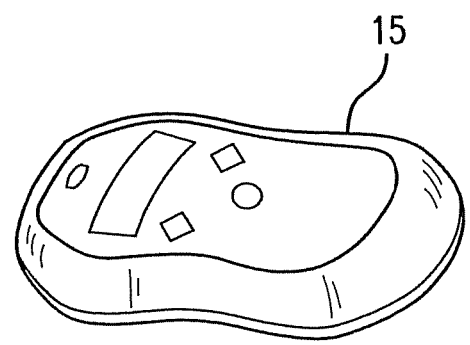
FIG. 6 is a top view of a programmable controller for use with light therapy apparatus.

FIG. 6 illustrates a programmable controller 15 of a type that may be used to control the operation of light therapy apparatus 2 (or other light therapy apparatus as described below). Programmable controller 15 may be a separate, remote unit or may be directly connected to or integrated with light source 4. Programmable controller 15 may comprise a microprocessor, data store, power supply, clock and associated electronic circuitry. Control parameters are stored in the data store. Programmable controller 15 operates light source 4 according to the parameters in the data store. The parameters may specify one or more of:

treatment duration;
light intensity during the treatment;
whether light emitters operate continuously or are pulsed;
if the light emitters are pulsed, the rate at which light emitters are pulsed;
if the light emitters are pulsed, the duty cycle at which the light emitters are pulsed;
etc.

If light therapy apparatus has sets of light emitters having different characteristics (e.g. sets of LED that emit light at different wavelengths or sets of light emitters that illuminate target tissues in different locations) then separate control parameters may be provided for different sets of the light emitters. In some embodiments, different sets of parameters are specified for different segments (intervals) of a light treatment. For example, light therapy treatments may be defined for a set of intervals each lasting from a few seconds to a few hundred seconds or a fraction of an hour. Different parameters may be specified for each of the intervals. The intervals are not necessarily equal in length.

In some embodiments, different sets of parameters may be specified for different areas of light source 4. In some cases, some areas of light source 4 may be turned off because the treatment plan for a patient does not require light to be delivered at locations corresponding to those parts of the light source 4.

A physician, dentist, or therapist may program a patient's treatment regimen into programmable controller 15. This may be done, for example, with the aid of suitable software running on a computer that is in data communication with programmable controller 15 or by way of a suitable user interface built into programmable controller 15.

Programmable controller 15 may have one or more pre-set programs built in. As an alternative to, or as an aid to programming controller 15 the physician, dentist, or therapist may select a pre-set program that is appropriate for controlling light therapy apparatus 2 to deliver light to a patient.

A typical treatment regimen provides a dose of light daily. Each of the daily doses of light may be delivered over a period lasting between a few minutes and an hour or so. For example, the inventor has found that daily ½ hour doses of light can be effective and are not unduly inconvenient for patients. A single daily dose appears to be as effective as dividing the same dose into multiple sessions delivered at different times during the day. Examples of possible treatment regimens are:

Enhancement of bone density by applying light in 5 treatments per week for 12 weeks. Each treatment lasts ½ hour and illuminates the tissues of a patient's jaw with light having wavelengths of 660 nm and 840 nm. The 660 nm light has an intensity of about 20 mW/cm$^2$ at the skin's surface The 840 nm light has an intensity of about 10 mW/cm$^2$ at the skin's surface.

Accelerating healing of bone grafts by applying light in daily treatments for 21 days. Each treatment lasts between 20 minutes and one hour and illuminates the tissues of a patient's jaw with light having a wavelength of 618 nm and an intensity of 20 mW/cm$^2$ at the skin's surface.

Programmable controller 15 may maintain a log of treatments that have been delivered. For example, controller 15 may log the date and time that each treatment was initiated, the duration of the treatment, and whether or not the treatment was completed. This log can be subsequently reviewed by a dentist, physician, or the like to evaluate whether or not the patient has complied with the prescribed treatment regimen.

Programmable controller 15 has a button or other suitable user patient interface that allows a patient to initiate a treatment according to previously-set parameters in the data store. The patient interface is preferably very simple such that minimal instruction is required to explain to a patient how to use light therapy apparatus 2. Programmable controller 15 may include an audible or visual indicator that generates a signal to remind a patient that it is time for a treatment (or that a scheduled treatment is overdue).

A patient can use light therapy apparatus 2 at home or in another location by operating programmable controller 15 to initiate delivery of a treatment.

Programmable controller 15 may comprise circuitry that monitors temperature at one or more locations in light source 4. The circuitry may monitor a signal modulated by a temperature sensor in light source 4. In the alternative, programmable controller 15 may monitor the current and voltage driving LEDs in light source 4. The current/voltage relationship is temperature-dependent. Thus, by monitoring the current/voltage relationship programmable controller 15 can determine whether the LED is at an undesirably high temperature. Programmable controller 15 may shut off or reduce current to light source 4 (or part of light source 4) when it detects that the temperature of light source 4 is undesirably high (or is trending towards being undesirably high). If light source 4 is equipped with a cooling fan then programmable controller 15 may optionally control the speed of the cooling fan in response to the monitored temperature.

Programmable controller 15 may be configured to maintain a log of treatments delivered by light therapy apparatus 2. The log may be reviewed by a physician, dentist or technician to verify that light therapy device has been used as prescribed by a patient. The log may track the times and durations of light therapy treatments delivered by light therapy apparatus 2 and may also track other features such as operating temperatures, operational status and the like.

Figure 7:
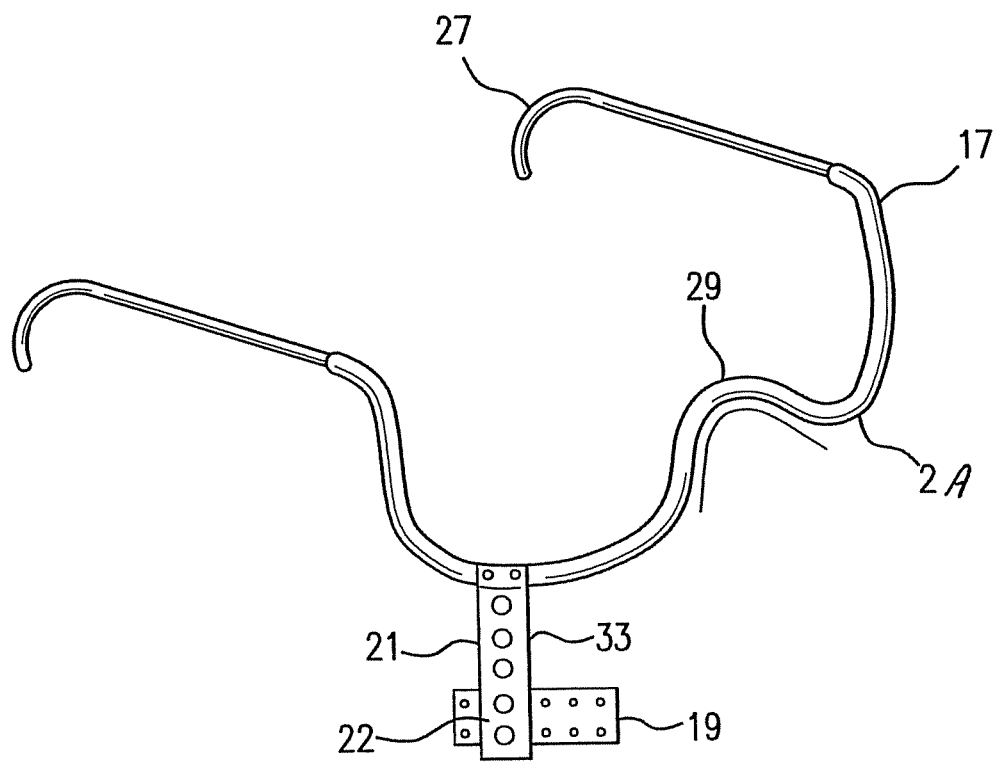
FIG. 7 is a perspective view of a light therapy device according to an alternative embodiment in which an LED array is supported by a head-set.
Figure 8:
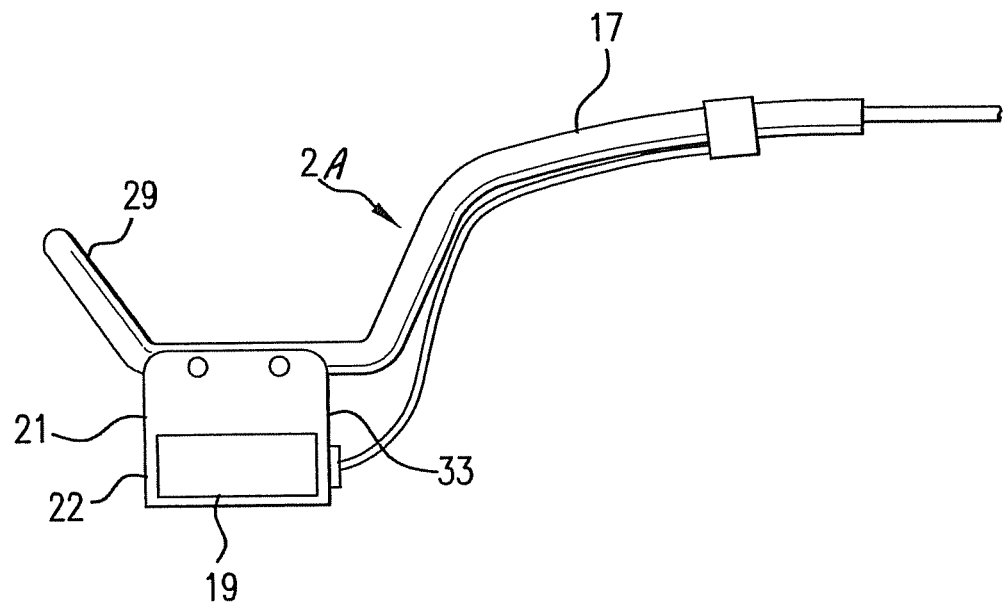
FIG. 8 is a side view of the light therapy device of FIG. 7.

FIGS. 7 and 8 show a light therapy apparatus 2A having a head-set style arrangement. Light therapy apparatus 2A comprises a head-set 17 and at least one extra-oral light source 19 mounted to head-set 17 by way of a suitable connector 21. Head-set 17 may have the general form of a frame for eyeglasses. In the illustrated embodiment, headset 17 has arms 27 that fit above and around the patient's ears and a frame 29 that fits over the bridge of the patient's nose. Head-set 17 may also include lenses (not shown). Suitably, the lenses may be made of a material that blocks radiation at wavelengths emitted by light source 19 so that the patient's eyes are protected from the radiation. Light source 19 may comprise an array of LEDs or other light emitters.

When head-set 17 has been adjusted to fit an individual patient, frame 29 registers with the bridge of the patient's nose and arms 27 sit on the patient's ears. Head-set 17 will sit on the patient's head in the same way each time it is put on. Head set 17 may be adjusted for fit by adjusting arms 27 which may be made of a firm, resilient material that allows for some flexibility for a better and more secure fit for individual users. In some embodiments, arms 27 can also be adjusted horizontally along their axis. Frame 29 can also be adjustable, for example, by bending to allow for a better and more secure fit. An elastic keeper such as an elastic strap may be provided to hold head-set 17 in place during use.

Figure 7A:
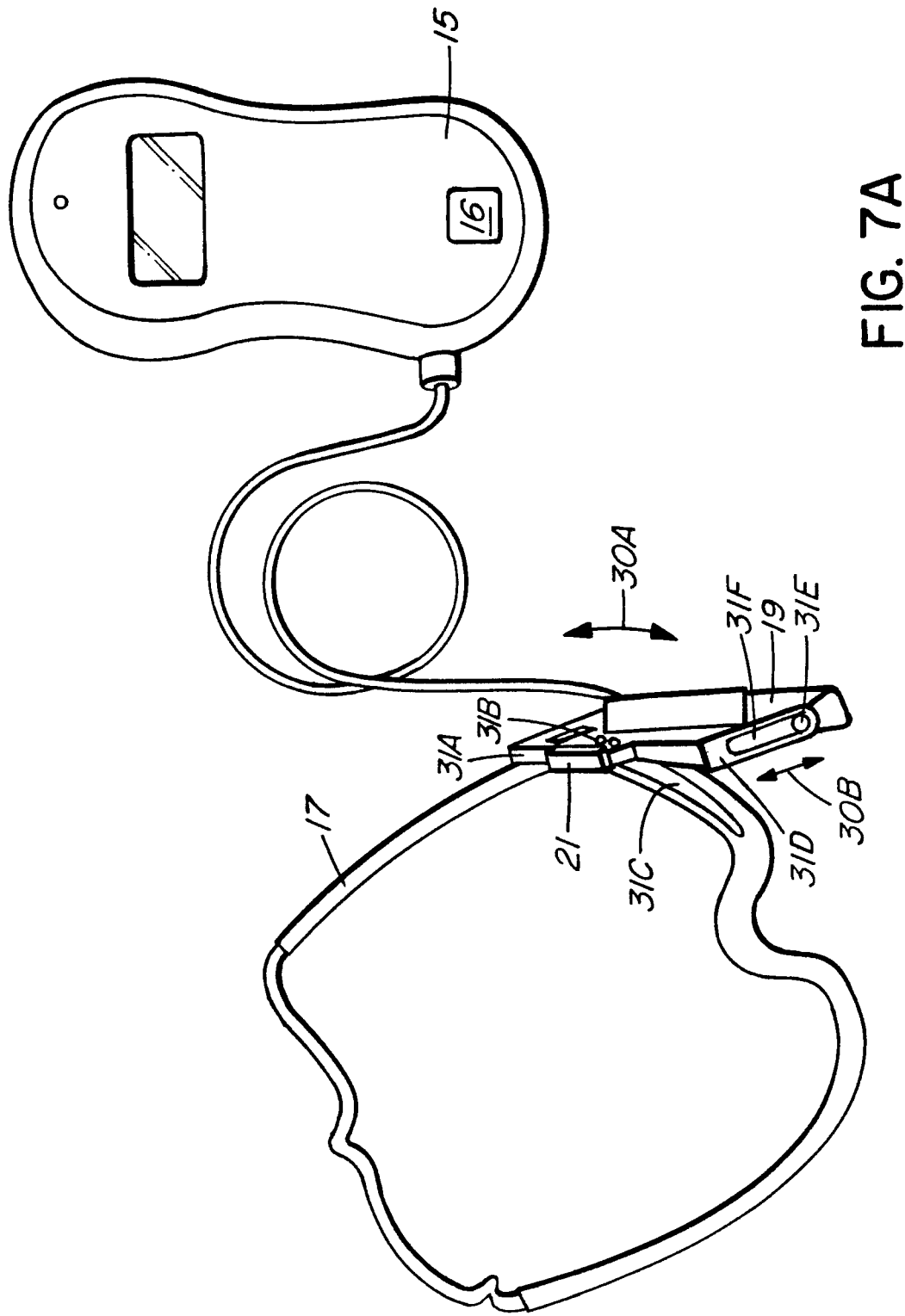
FIG. 7A is a perspective view of a light therapy device according to another alternative embodiment in which an LED array is supported by a head-set.

In the embodiment shown in FIG. 7A, connector 21 permits the position of light source 19 to be adjusted both along a horizontal axis 30A and a vertical axis 30B relative to head-set 17. A yoke 31A is mounted to head-set 17 by screws 31B which pass through slot 31C. The position of light source 19 in horizontal direction 30A can be adjusted by loosening screws 31B, sliding yoke 31A to a desired position along slot 31C and retightening screws 31B. Light source 19 is connected to arms 31D of yoke 31A by screws 31E which pass through slots 31F. The vertical position of light source 19 may be adjusted by loosening screws 31E, sliding light source 19 up or down along slots 31F to a desired vertical position and then retightening screws 31E.

In the illustrated embodiment slot 31C is curved when viewed from above. Slot 31C generally follows the curvature of a typical maxillary bone such that light source 19 can effectively be applied against the patient's skin for a range of positions of light source 19 along slot 31C. Since the lower portions of people's faces are typically narrower than upper portions, connector 21 may hold light source 19 so that it is tilted with its lower edge projecting more in the direction of the patient than its upper edge. In some embodiments the angle of tile of light source 19 is adjustable. Head-set 17 may be adjusted so that light source 19 is biased against the patient's face when head set 17 is being worn by a patient.

Many alternative designs for connector 21 may be provided. For example, connector 21 may comprise a bar, rod or similar device that can be clamped or otherwise fastened to head-set 17 and a clip or similar mechanism that fastens light source 19 to the bar, rod or similar device.

Figure 9:
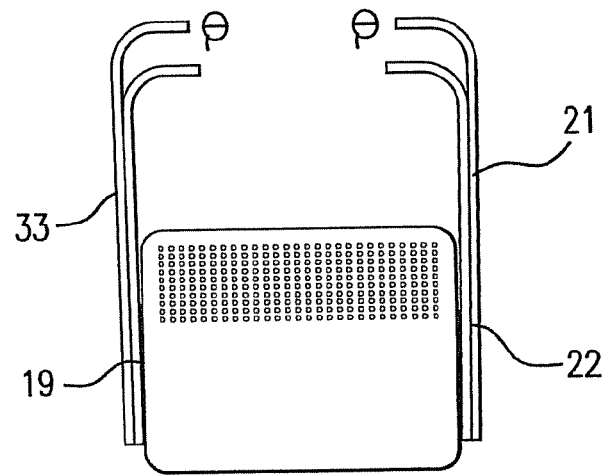
FIG. 9 is a front view of at least one LED array, and a connector detached from the head-set.

As shown in FIG. 9, in some embodiments light source 19 can be removably detached from head-set 17. This can be convenient for storage or transportation of light therapy apparatus 2A.

In another embodiment, head-set 17 comprises an adjustable strap (not shown) which fits around the crown of a patient's head for securing the extra-oral light therapy device 2A. The adjustable strap can also fit around a patient's chin and extend back to the crown and around the crown of a patient's head. The adjustable strap may be made of a flexible, elastic woven material.

Figure 10:
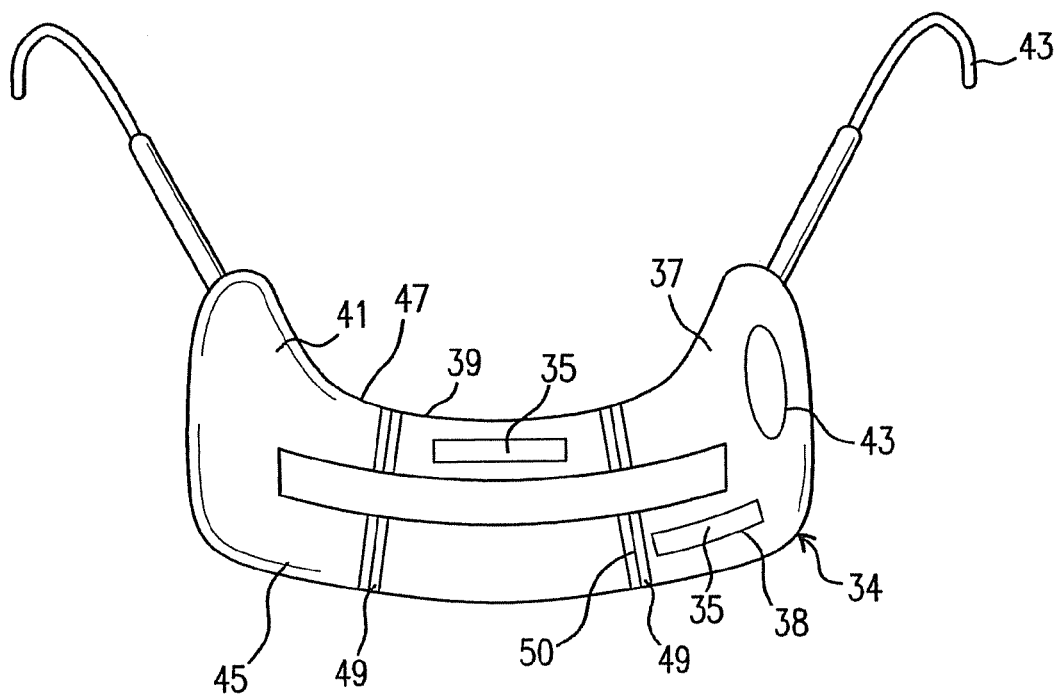
FIG. 10 is a front view of an external light therapy device having two LED arrays, a hinge-like member, and an attaching means.

FIG. 10 shows a light therapy apparatus 34 comprising at least one light source 35. Light source 35 comprises at least one light emitter, for example an LED array, mounted on a thin molded substrate 51 (FIG. 11). More than one array of light emitters may be provided in light source 35. For example, the light source 35 shown in FIG. 10 has two arrays of LEDs. Arrays 36 of light emitters may be arranged in lower level 45 and an upper level 47. The upper and lower levels may be separately controlled. The upper and lower levels respectively irradiate tissues of the upper and lower jaws. An attaching means 43 is provided for securing the device to the area of treatment.

A power source and controller, which may comprise a programmable controller 15 as described above, operate light source 35 to emit light according to a desired protocol.

In the example apparatus 34 shown in FIG. 10, light source 35 has a right section 37, a center section 39 and a left section 41. Right section 37 and the left section 41 are respectively supported on the right and left sides of a patient's face. A light source 35 as shown in FIG. 10 may be supported by way of any suitable attaching means including:
- a head-set 17 as described above;
- an intra-oral tray 7 which may comprise a full tray or one or more bite tabs as described above;
- an adhesive such as double-sided adhesive tape;
- a strap or set of straps; or
- the like.

The LED arrays may be removably attached to light source 35 by suitable connectors 38 such as ribbon connectors or may be more permanently integrated into light source 35 as illustrated in FIG. 11. Providing removable, repositionable LED arrays on a light source 35 permits LED arrays to be arranged on light source 35 so as to optimally illuminate target tissues. LED arrays may be concentrated to illuminate target tissues while areas of light source 35 that overly non-target tissues do not need to have any LED arrays.

Figure 12:
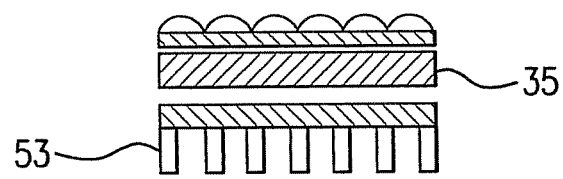
FIG. 12 is a cross-sectional view of an LED array detached from the substrate.

FIG. 12 shows a cross-section of an LED array 36 of external light therapy device 34 detached from substrate 51. A clip or similar attaching means 53 allows the at least one LED array 36 to be mounted onto substrate 51. Substrate 51 serves as a heat sink as described above. Substrate 51 may be made of aluminum or similar metal that is a good heat conductor. Substrate 51 may be moldable (i.e. flexible in one or two dimensions so that it can be formed to follow contours of a patient's face and, once formed, will retain its shape).

Hinge-like members 49 may be provided between arrays 36 to allow light source 35 to be bent to provide a better fit around the facial area. Hinge-like member 49 may comprise a thin crease 50 or other bend line set into the substrate material, as illustrated in FIG. 11. Hinge-like member 49 allows the center section 39 to fit around a patient's mouth and the right section 37 and the left section 41 to fit around a patient's face.

Apparatus as described herein may be applied to treat a variety of conditions including:
- jaw osteonecrosis,
- other jaw bone disorders,
- periodontitis,
- malocclusion and other conditions treated by orthodontics,
- stimulation and acceleration of healing after oral surgery or periodontal surgery,
- stimulation of the healing of wounds at the locations of bone grafts,
- healing and acceleration of osseo-integration of endosseous dental implants; and,
- the like.

The application to jaw osteonecrosis permits treatment of a condition for which existing treatments are highly invasive. Treating osteonecrosis using light therapy is significantly more cost-effective and comfortable for the patient than existing surgical treatment options.

The apparatus may be applied by fitting a support to a patient. The support may comprise a head-set, intra-oral tray, a bite tab, or the like. When the support has been fitted so that it can be repeatably worn by the patient one or more light sources are mounted to the support at locations where light from the light sources can illuminate a treatment area. A treatment regimen is then established. The physician, dentist, or therapist at his office or a patient at his home then performs the prescribed extra-oral light therapy treatment.

An example method for treatment for jaw osteonecrosis, other jaw bone disorders, periodontitis, orthodontics, or for stimulation and acceleration of healing after oral surgery or periodontal surgery or for acceleration of osseo-integration of endosseous dental implants applies extra-oral light therapy device 2. Prior to extra-oral light therapy treatment, intra-oral tray 7 is prepared by filling it with a suitable settable material such as a clear vinyl siloxane gel or similar material. The intra-oral tray is then placed around the patient's teeth to obtain an impression of the patient's teeth. After the settable material sets, intra-oral tray 7 can be used to achieve consistent targeting of light to target tissues bone during subsequent treatments.

A physician, dentist, or therapist programs a patient's prescribed treatment regimen into a programmable controller 15 (see FIG. 6, for example). Programmable controller 15 controls parameters of a light therapy treatment to be delivered by light therapy apparatus 2. For example, controller 15 may control the duration of the treatment, light intensity, pulse frequency, etc. Programmable controller 15 runs a patient's prescribed treatment regimen causing the at least one light source 4 to emit pulsed or continuous light according to the prescribed parameters onto the treatment area. Therefore, stimulating and accelerating bone formation and healing at a patient's treatment area for the treatment of jaw bone disorders and jaw osteonecrosis.

The invention also relates to a method for the treatment and stimulation of soft and hard tissue and the biostimulation of bone. In this method, a light source 35 which may comprise at least one LED array 36 is first attached to the desired area of treatment. A physician, dentist, or therapist programs a patient's prescribed treatment regimen into a programmable controller 15. Programmable controller 15 controls the energy density, pulse frequency and duration of the external light therapy device 34. The programmable controller 15 runs a patient's prescribed treatment regimen causing the at least one LED array 35 to emit pulsed or continuous light at the predetermined rates and frequencies onto the treatment area. The light therapy device can provide effective, stabilized, repeatable, accurate, programmable, and consistent light therapy for the treatment and stimulation of soft and hard tissue and the biostimulation of bone.

Several studies have been carried out to determine the effectiveness of the invention. In one, a retrospective record review of a cohort of 68 QUS (quantitative ultrasound) scanned dental patients from the private practices of two co-investigators as performed. All scans and treatments occurred between 2002 and 2005. Inclusion criteria included: 1) no surgical procedure at an investigative site during or less than one year prior to entry into the study; 2) pre-treatment and post-treatment QUS scans of the maxillofacial region; 3) LED therapy to one or more maxillofacial regions. Exclusion criteria included: 1) a medical condition associated with abnormal bone growth or remodeling, such as Paget's disease of bone, fibrous dysplasia, osteopetrosis, severe systemic osteoporosis, etc.; 2) unwillingness to sign informed consent form; 3) inability to perform daily LED treatments at home; 4) inability to obtain high quality QUS scans of the jaws. An exclusion waiver for the research was provided by the Committee for the Protection of Human Subjects of the University of Texas in Houston and informed consent was obtained from all subjects.

QUS scans were made immediately prior to LED therapy and immediately thereafter. All scans were performed by the FDA cleared dental QUS device, the Cavitat 4000™ (Cavitat Medical Technologies, Inc, Aurora, Colo.). This device renders a series of 3-dimensional cube images from analog signals generated when an external transmitter sends 27,000 sound pulses per microsecond through the alveolar bone at a speed of 317.6 meters per second, 3.5 mHz, to an intraoral piezo screen held on the lingual aspect of the alveolus. The screen has 64 sensors which detect electrical changes in the screen as sound distorts it. The test is premised on the assumption that sound traveling through LBD (low bone density) becomes attenuated, hitting the receptor screen with less intensity than sound which has traveled through normal bone. The speed of sound is also diminished and so changes in speed are captured and accounted for by the device.

All initial and follow-up QUS scans of alveolar bone were blindly and independently graded, after calibration, by two investigators according to an established 5-point scale, and the following results were shown (Table 1):

TABLE 1

Grading categories for individual 3-D cube images (64 columns in each) of the Cavitat QUS images.

| QUS Grade * | Description ** |
|---|---|
| 0 | "Green bone." Cube shows no loss of column height and is 100% green; or mild loss of column height in less than ¼ of columns (16 columns); and/or moderate to severe loss of column height in less than 4 non-adjacent columns. |
| I | Cube shows mild loss of column height in more than ¼ of columns; and/or moderate loss of column height in ¹⁄₁₆ to ¼ of the columns (5-16 columns); and/or severe loss of height in ¹⁄₁₆ to ⅛ of the columns (5-8 columns). |
| II | Cube shows moderate loss of column height in ¼ to ½ of columns (17-32 columns); and/or severe loss of height in ⅛ to ¼ of columns (8-16 columns). |
| III | Cube shows moderate loss of column height in more than ½ of columns (32 columns); and/or severe loss of column height in ¼ to ½ of columns (17-32 columns). |
| IV | Cube shows severe loss of column height in more than ½ of columns (32 columns). |

* high grade lesion = Grade III and IV scans; low-grade lesion = Grade I and II scans; "green bone" = normal or Grade 0 scan
** definition of loss of column height: mild (crown is green, less than ⅓ loss of height); moderate (crown is yellow or brown, ⅓ to ⅔ loss of height); severe (crown is orange or red, more than ⅔ loss of height)

In case of differences, a consensus grade was arrived at via discussion between the two. QUS grades of positive scans, i.e. scans with grades I-IV before LED therapy were compared with post-therapy scan grades using matched pair analysis.

Patients were treated using the a device made in accordance with the present invention, the investigational OsseoPulse™ (Version 1.0) device (made by Biolux Research Ltd., Vancouver, Canada). The device consists of an extra-oral array of highly-efficient light emitting diodes (LED) producing non-coherent continuous wave monochromatic light in the visible far red (660 nm @ 15 mW/cm2) and infra-red range (840 nm @ 20 mW/cm2). In addition, there was an integral alignment device used to ensure that the LED array was repeatably and accurately positioned directly over the treatment sites. The OsseoPulse device was placed on the facial surface for 15 minutes daily, 5 days a week for 12 weeks on each treatment side. The dose per session per treatment area was approximately 200 Joules per square inch.

Of 1,148 pre-treatment QUS jawbone scans, each representing the area of one tooth, 294 were positive for damaged or abnormal bone. Using the 5-point scale (0=normal; 4=most severe), half of these sites were low grade, i.e. grades 1 or 2, with half being high grade (Table 2):

TABLE 2

Results of 294 QUS scans before and after 3 months of daily LED photobiomodulation.

| Grade Level * | # at Pre-Treatment | # at Post-Treatment |
|---|---|---|
| 1 | 79 | 120 |
| 2 | 69 | 54 |
| 3 | 86 | 53 |
| 4 | 61 | 40 |
| Mean: | 2.43 | 1.33 |

* 1 = mild LBD/dehydration; 4 = severe LBD/dehydration

The average grade for all 294 positive sites was 2.43. After LED photomodulation the average grade was 1.33 and almost 42% of investigated sites had returned to completely normal bone, while another 54 (18.4%) sites were grade 1 after therapy (Table 2). One would expect that the lower the pre-treatment grade, the larger would be the proportion which returned to normal, since it takes a much greater grade improvement to reach normal from the higher grades. This proved to be the case: regions with pre-treatment grades of 1, 2, 3 and 4 returned to green bone 68.4%, 46.4%, 30.2% and 13.3% of the time, respectively (Table 3):

TABLE 3

Post-treatment changes for each pre-treatment grade level, 294 QUS scans.

| Grade Level* | Number of Sites at Pre-Treatment | Number @ Grade for each Site at Post-Treatment* | | | | | Avg. Change |
|---|---|---|---|---|---|---|---|
| | | 0** | 1** | 2** | 3** | 4** | |
| 1 | 79 | 54 | 15 | 8 | 2 | 0 | −0.54 |
| 2 | 69 | 32 | 19 | 12 | 4 | 2 | −1.32 |
| 3 | 86 | 26 | 17 | 22 | 16 | 5 | −1.50 |
| 4 | 60 | 8 | 3 | 10 | 18 | 21 | −1.32 |
| Mean: | 2.43 | 120 | 54 | 52 | 40 | 28 | −1.11 |

*1 = mild LBD/dehydration; 4 = severe LBD/dehydration (see Table 1)
**Represents grade levels, 0-4, as described in Table 1

Almost 71% of the 294 treated sites demonstrated improvement of at least one QUS grade level, with most of those, 43.4%, dropping by one grade. The post-treatment grade change was relatively uniform all each pretreatment QUS grade level (Table 3). Overall the mean difference, i.e. improvement of bone quality, of −1.11 was very statistically significant (matched pair analysis: Std error 0.06914; t-Ratio −15.9896; DF 293; prob [t] less than 0.0001; 95% confidence interval 0.558-1.242).

While in the foregoing specification this invention has been described in relation to certain preferred embodiments thereof, and many details have been set forth for the purpose of illustration, it will be apparent to those skilled in the art that the invention is susceptible to additional embodiments and that certain details described herein can be varied considerably without departing from the basic principles of the invention. For example:

- Light therapy apparatus 34 may be applied for treatment and stimulation of other bone or soft tissues, such as the hip. In such applications, light source 35 can be attached to a treatment area with an adhesive such as double-sided adhesive tape (not shown). Alternatively, the external light therapy apparatus 34 can be placed or sewn into a pouch, undergarment or similar garment and attached to the treatment area through means of a strap, button or similar attaching means (not shown).
- It is not mandatory that a controller be programmable. For example, a controller may have controls that allow various parameters to be set. A physician, therapist or technician may set those controls so that an appropriate treatment is delivered when a patient initiates delivery of the treatment.
- Features or components described in relation to one of the embodiments described herein may be provided in combination with components or features of other ones of the example embodiments described herein. For example, the controller 15 shown in FIG. 6 could be used in conjunction with any of the described embodiments. Light sources having a property or properties like those of the light source 4 shown in the embodiments of FIGS. 1 to 1C could be applied in other embodiments.

It is therefore intended that the following appended claims and claims hereafter introduced are interpreted to include all such modifications, permutations, additions and sub-combinations as are within their true spirit and scope.

What is claimed is:

1. A light therapy apparatus comprising:
    a support configured to register with one or more anatomical features of a patient's head, the support defining a first slot along a first axis
    a yoke that is mounted along the support, the yoke being slidably coupled to the support via a first fastener movable within the first slot, the yoke defining a second slot along a second axis; and
    at least one extra oral light source slidably coupled to the yoke via a second fastener movable within the second slot, the light source configured to apply against the skin of the patient over a jaw bone of the patient when the apparatus is worn by the patient, the slidable coupling of the yoke and the slidable coupling of the light source allowing the light source to be adjusted along the first axis and the second axis, the extra-oral light source configured to irradiate light through the patient's skin toward a region of the jaw bone of the patient in an amount that is effective for at least one of a treatment of a bone disorder or biostimulation of at least one of bone or soft tissue.

2. The light therapy apparatus of claim 1, wherein the at least one light source includes an extra-oral LED array.

3. The light therapy apparatus of claim 1, further comprising:
    a controller configured to provide a voltage to the light source effective for phototherapy and configured to control at least one of the energy density, the pulse frequency, or the duration of the light.

4. The light therapy apparatus of claim 3, wherein the controller is programmable and is configured to control light output by a first group of light emitters and a second group of light emitters in the light source.

5. The light therapy apparatus of claim 3, wherein the controller is configured to determine a temperature at the light source and configured to discontinue operation of the light source when the temperature exceeds a threshold temperature.

6. The light therapy apparatus of claim 3, wherein the controller is configured to maintain a log of treatments delivered by the light therapy apparatus.

7. The light therapy apparatus of claim 3, wherein the controller is configured to store a treatment regimen including scheduled treatments and includes an indicator that is configured to generate a signal to remind a patient of at least one of the scheduled treatments, the controller being capable of operating in response to the stored treatment regimen.

8. The light therapy apparatus of claim 3, wherein the controller is a remote unit and is separate from the support.

9. The light therapy apparatus of claim 1, wherein the light source includes a plurality of emitters configured to emit light in the wavelength range of about 620 nm to about 680 nm or about 820 to about 890 nm.

10. The light therapy apparatus of claim 9, wherein the plurality of emitters configured to emit light in at least one of the wavelength ranges:
    613 nm to 624 nm,
    667 nm to 684 nm,
    750 nm to 773 nm, and
    812 nm to 846 nm.

11. The light therapy apparatus of claim 9, wherein the plurality of emitters configured to emit light of a wavelength corresponding to an absorption band of cytochrome c oxidase.

12. The light therapy apparatus of claim 11, wherein the absorption band is an absorption band of reduced cytochrome c oxidase.

13. The light therapy apparatus of claim 11, wherein the absorption band is an absorption band of oxidized cytochrome c oxidase.

14. The light therapy apparatus of claim 1, wherein the support includes a head set having a frame configured to register with a bridge of a patient's nose.

15. The light therapy apparatus of claim 14, wherein the head set includes a pair of arms extending rearwardly from the frame, the arms configured to sit on the patient's ears.

16. The light therapy apparatus of claim 1, wherein the yoke is configured to be repositioned along the support in a substantially horizontal direction along the first axis and the light source is configured to be repositioned along the yoke in a substantially vertical direction along the second axis.

17. The light therapy apparatus of claim 1, wherein the light source is configured to contact a side of the patient's face when the apparatus is worn by the patient.

18. The light therapy apparatus of claim 1, wherein the first fastener includes a first screw and the second fastener includes a second screw.

19. The light therapy apparatus of claim 18, wherein a horizontal position of the yoke is configured to be adjusted by loosening the first screw, moving the yoke to a desired position, and retightening the first screw.

20. The light therapy apparatus of claim 18, wherein a vertical position of the at least one light source is adjusted by loosening the second screw, moving the light source, and retightening the second screw.

21. The light therapy apparatus of claim 1, wherein the at least one light source includes emitters of light having an average light intensity of at least about 10 mW/cm$^2$.

22. The light therapy apparatus of claim 1, wherein the at least one light source includes emitters of light having an average light intensity in the range of 10 mW/cm² to about 60 mW/cm².

23. The light therapy apparatus of claim 1, wherein the at least one light source includes emitters of light having an average light intensity in the range of 20 mW/cm² to about 60 mW/cm².

24. The light therapy apparatus of claim 1, wherein the at least one light source includes emitters of light having a peak light intensity higher than 50 mW/cm².

25. The light therapy apparatus of claim 1, further comprising:
a cooling system configured to dissipate heat.

26. The light therapy apparatus of claim 25, wherein the cooling system is configured for at least one of forced air or liquid cooling.

27. The light therapy apparatus of claim 25, wherein the cooling system includes a heat sink.

28. The light therapy apparatus of claim 1, wherein the at least one light source further comprises at least one of optics or reflectors that are configured to direct the light emitted from the light source.

29. The light therapy apparatus of claim 28, wherein the at least one of optics or reflectors are encapsulated in plastic.

30. The light therapy apparatus of claim 1, wherein the support is composed of a material that allows for flexibility and customization for differing patient face morphology.

31. The light therapy apparatus of claim 1, wherein the at least one light source is biased against the patient's face when the apparatus is worn by the patient.

32. The light therapy apparatus of claim 1, wherein the first axis is a central axis of the support.

33. The light therapy apparatus of claim 32, wherein:
the support is curved such that the central axis follows a curvature of a maxillary bone.

34. A light therapy apparatus comprising:
a support including a head set having a frame configured to register with a bridge of a patient's nose and a pair of arms extending rearwardly from the frame, the support defining a first slot having a curvature that substantially follows a curvature of a maxillary bone;
a yoke slidably coupled to the support along the first slot such that the yoke is repositionable relative to the support along a length of the first slot, the yoke defining a second slot, the second slot being transverse to the first slot; and
at least one extra-oral light source configured to be slidably coupled to the yoke along the second slot, the light source being repositionable relative to the yoke along a length of the second slot, the head set configured such that the at least one extra-oral light source is biased against a face of the patient when the apparatus is worn by the patient, the extra-oral light source configured to irradiate light through the patient's skin toward a region of the jaw bone of the patient in an amount that is effective for at least one of a treatment of a bone disorder or biostimulation of at least one of bone or soft tissue.

35. The light therapy apparatus of claim 34, wherein the frame has a size such that the frame does not extend in front of the patient's eyes when the apparatus is worn by the patient.

36. The light therapy apparatus of claim 34, wherein the first slot is along a central axis of the support.

\* \* \* \* \*